(12) United States Patent
Hieb et al.

(10) Patent No.: US 8,147,463 B2
(45) Date of Patent: Apr. 3, 2012

(54) FLUID PURGE IN A MEDICAL INJECTION SYSTEM

(75) Inventors: Martin G Hieb, St. Louis Park, MN (US); Khader Mohiuddin, Medina, MN (US); Sidney D Nystrom, Shoreview, MN (US); Robert F Wilson, Roseville, MN (US)

(73) Assignee: ACIST Medical Systems, Inc., Eden Praire, MN (US)

( * ) Notice: Subject to any disclaimer, the term of this patent is extended or adjusted under 35 U.S.C. 154(b) by 355 days.

(21) Appl. No.: 12/303,657

(22) PCT Filed: May 29, 2007

(86) PCT No.: PCT/US2007/069834
§ 371 (c)(1),
(2), (4) Date: Dec. 5, 2008

(87) PCT Pub. No.: WO2007/146586
PCT Pub. Date: Dec. 21, 2007

(65) Prior Publication Data
US 2010/0200076 A1    Aug. 12, 2010

Related U.S. Application Data

(60) Provisional application No. 60/804,682, filed on Jun. 14, 2006.

(51) Int. Cl.
*A61M 5/00* (2006.01)
(52) U.S. Cl. ............... 604/247; 604/246; 604/256
(58) Field of Classification Search ............ 604/167.01, 604/167.03, 167.04, 246, 247, 256
See application file for complete search history.

(56) References Cited

U.S. PATENT DOCUMENTS

| | | | | |
|---|---|---|---|---|
| 4,044,757 A | * | 8/1977 | McWhorter et al. | 600/432 |
| 4,084,606 A | * | 4/1978 | Mittleman | 137/102 |
| 4,462,409 A | * | 7/1984 | Pace et al. | 600/488 |
| 4,819,684 A | * | 4/1989 | Zaugg et al. | 137/112 |
| 5,097,841 A | * | 3/1992 | Moriuchi et al. | 600/488 |
| 5,176,658 A | * | 1/1993 | Ranford | 604/247 |
| 6,182,698 B1 | * | 2/2001 | Barak | 137/845 |
| 6,254,835 B1 | | 7/2001 | Feygin | |
| 6,569,117 B1 | * | 5/2003 | Ziv et al. | 604/164.01 |
| 6,638,258 B2 | * | 10/2003 | Schwartz et al. | 604/247 |

(Continued)

OTHER PUBLICATIONS

"PCT International Search Report for PCT/US2007/069834 dated Aug. 13, 2008, from which the instant application is based," 4 pgs.

(Continued)

*Primary Examiner* — Nicholas Lucchesi
*Assistant Examiner* — Victoria P Campbell
(74) *Attorney, Agent, or Firm* — Fredrikson & Byron, P.A.

(57) ABSTRACT

One embodiment of the invention provides a method to purge air or liquid from a powered injection system. In this embodiment, the method includes driving a first pumping device in a first operational mode to inject an amount of a first liquid medium through disposable tubing and a disposable valve, driving the first pumping device in a second operational mode to deform the disposable valve, and driving a second pumping device to inject an amount of a second liquid medium through the disposable tubing and the deformed valve. In one embodiment, the first pumping device comprises a first syringe, the second pumping device comprises a second syringe, and the disposable valve comprises an elastomeric valve.

10 Claims, 24 Drawing Sheets

U.S. PATENT DOCUMENTS

| | | | |
|---|---|---|---|
| 6,708,714 B1* | 3/2004 | Mijers | 137/102 |
| 7,389,788 B2* | 6/2008 | Wilson et al. | 137/112 |
| 7,581,559 B2* | 9/2009 | Bausmith, III | 137/512 |
| 7,610,936 B2* | 11/2009 | Spohn et al. | 137/877 |
| 7,617,837 B2* | 11/2009 | Wilson et al. | 137/112 |
| 2003/0122095 A1 | 7/2003 | Wilson et al. | |
| 2005/0230575 A1* | 10/2005 | Zelenski et al. | 248/176.1 |
| 2005/0234407 A1* | 10/2005 | Spohn et al. | 604/253 |
| 2005/0234428 A1* | 10/2005 | Spohn et al. | 604/533 |
| 2006/0167415 A1* | 7/2006 | Nemoto | 604/154 |
| 2006/0178632 A1* | 8/2006 | Trombley et al. | 604/151 |
| 2006/0180202 A1* | 8/2006 | Wilson et al. | 137/112 |
| 2007/0161970 A1* | 7/2007 | Spohn et al. | 604/533 |
| 2007/0167919 A1* | 7/2007 | Nemoto et al. | 604/189 |
| 2007/0244435 A1* | 10/2007 | Hicks | 604/131 |
| 2008/0086087 A1* | 4/2008 | Spohn et al. | 604/151 |
| 2008/0161634 A1* | 7/2008 | Nemoto et al. | 600/5 |
| 2008/0300483 A1* | 12/2008 | Nemoto et al. | 600/431 |
| 2010/0019178 A1* | 1/2010 | Wilson et al. | 251/61.1 |

OTHER PUBLICATIONS

"PCT Written Opinion for PCT/US2007/069834 dated Aug. 13, 2008, from which the instant application is based," 4 pgs.

* cited by examiner

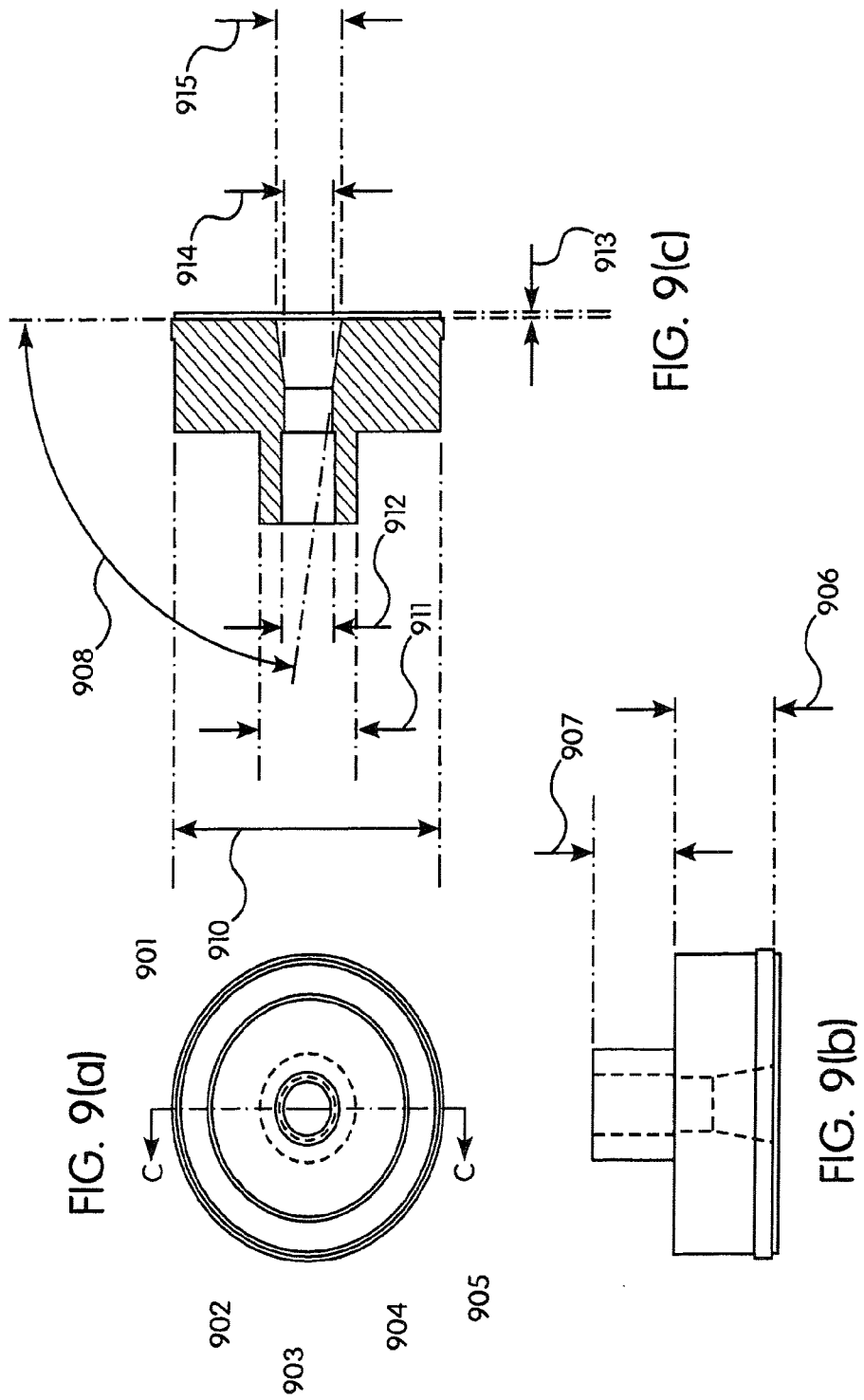

US 8,147,463 B2

FLUID PURGE IN A MEDICAL INJECTION SYSTEM

RELATED APPLICATIONS

This application claims priority to International Application No. PCT/US2007/069834 filed May 29,2007, and to U.S. Provisional Patent Application No. 60/804,682 filed Jun. 14, 2006, the teachings of which are incorporated herein by reference.

TECHNICAL FIELD

This application relates generally to the field of medical device technology and, in particular, to medical fluid injection systems that may be used for angiography, computed tomography (CT), or other medical procedures.

BACKGROUND

Certain medical procedures, such as, for example, contrast media injections during angiographic procedures, can require that liquids (such as radiographic contrast agents) be injected into a patient's vascular system under pressure. In certain cases, liquids may be injected at pressures as high as 1200 pounds per square inch (psi), or possibly even higher.

While performing such injection procedures, it may also be desirable to measure a patient's biological pressures for hemodynamic monitoring. For example, in angiography, it may be desirable to record intravascular and intracardiac pressures between high pressure injections of the contrast media. Pressure transducers that are designed for physiological measurements, such as hemodynamic measurements, often cannot tolerate even moderate injection pressures and therefore must typically be isolated from any high pressure flow during an injection.

SUMMARY

One embodiment of the invention provides a method to purge air or liquid from a powered injection system. In this embodiment, the method includes driving a first pumping device in a first operational mode to inject an amount of a first liquid medium through disposable tubing and a disposable valve, driving the first pumping device in a second operational mode to deform the disposable valve, and driving a second pumping device to inject an amount of a second liquid medium through the disposable tubing and the deformed valve. In one embodiment, the first pumping device comprises a first syringe, the second pumping device comprises a second syringe, and the disposable valve comprises an elastomeric valve.

In one embodiment, the type of valve that is used in the powered injection system is a deformable valve, such as an elastomeric valve. As used in the powered injection system, an elastomeric valve allows for forward liquid flow in one direction yet prevents backflow in the opposite direction. Before an elastomeric valve can be connected up to a patient, air on both sides of the valve should be removed, according to one embodiment. This application discloses methods that, when performed, help remove air from both sides of such a valve, according to some embodiments.

Various advantages and benefits are provided by certain embodiments of the invention. For example, certain embodiments help clear air bubbles from the line and minimize the amount of contrast needed during an injection procedure. In addition, certain embodiments may help a clinician position a catheter tip in a safe position, away from direct contact with the arterial lining of a patient, to help minimize the chance of complications, such as dissection or perforation of a vessel wall. The shape and fine structure content of hemodynamic signals returned through the fluid-filled catheter tip back to a pressure transducer aid the clinician in assessing the catheter's position for safe injections. Various embodiments help minimize signal dampening that may be caused by the presence of viscous contrast or air bubbles in the line.

BRIEF DESCRIPTION OF THE DRAWINGS

FIGS. 9(a)-(c) depict various views of an exemplary disc holder according to one embodiment of the present invention.

DETAILED DESCRIPTION

Figure 1:
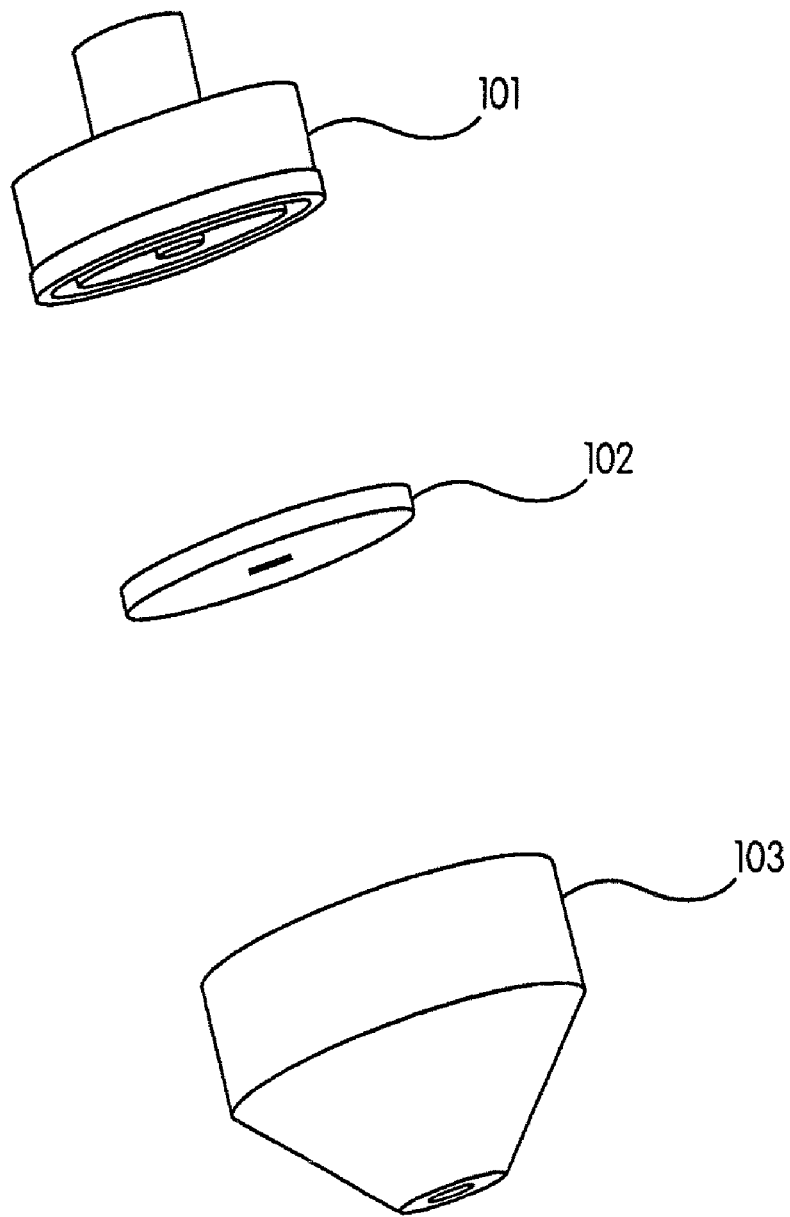
FIG. 1 is an expanded view of an exemplary valve assembly according to one embodiment of the present invention.

With reference to FIG. 1, an exemplary embodiment of a high-pressure activated valve will be described. An exemplary low and high-pressure elastomeric valve is comprised of a disc holder 101, a middle valve disc 102 and a valve body 103. The valve body 103 and disc holder 102 are made of a relatively rigid polymer, such as for example, polycarbonate, and the valve disc 102 is molded of an elastomer, preferably silicone rubber, with a slit in the center.

The elastomeric disc 102 with the slit is sandwiched between the valve body 103 and disc holder 101 and is affixed at the perimeter of the disc. Such affixation may be effected by, for example, entrapment, adhesion, mechanical or chemical welding, or any other means known in the art. The valve body 103 and disc holder 101 are bonded together, by, for example, sonic welding, UV curable adhesive, mechanical threads or snap (interference) locking, or other bonding or adhesion technologies as may be known in the art, thus entrapping the disc.

In an exemplary embodiment, the valve has at least two, and preferably three, ports that communicate with attached tubing. Such ports are, for example, (a) a contrast inlet port, (b) a saline inlet and pressure transducer port, and (c) a patient or outlet port. In an exemplary embodiment the disc holder 101 contains such a contrast inlet port, as is shown in more detail in FIG. 2, described next.

Figure 2:
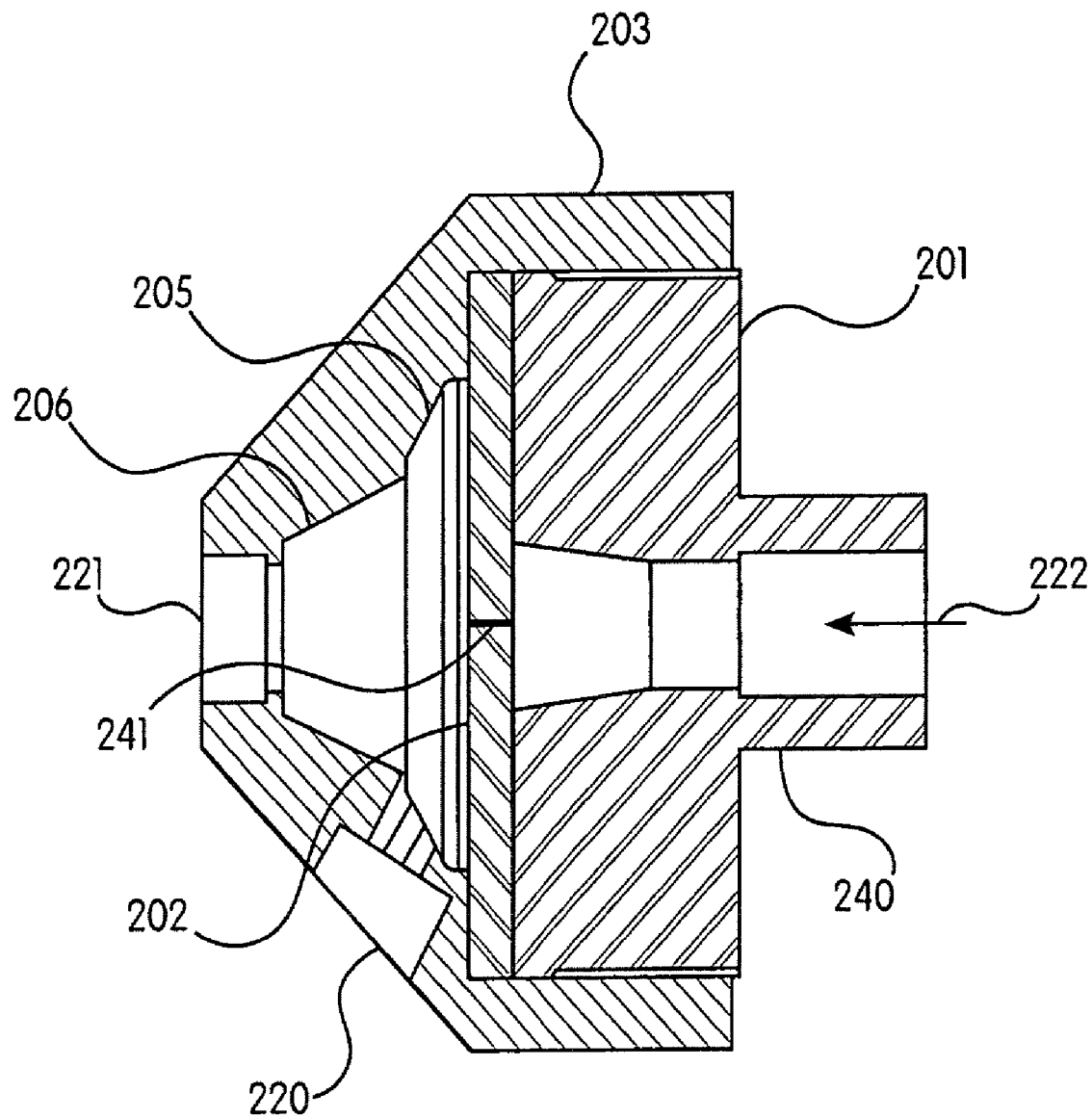
FIG. 2 is a cross sectional view taken along a direction normal to fluid flow of the exemplary valve assembly of FIG. 1 depicting the normal (low pressure) mode of operation.

With reference to FIG. 2, a valve body 203 contains a saline/transducer 220 and a patient/outlet 221 port. Also, a disc holder inlet port hole 222 is tapered outward (in the forward flow direction, i.e., from right to left in FIG. 2) to create a pocket 240 in front of an elastomeric disc 202 so that as fluid travels through the hole 222 and into the empty pocket, air is forced from the pocket (purged) through the disc slit 241 and into the valve body 203 (more precisely, into the cavity in the valve body which is adapted to fluid flow). Thus, for example, in an angiographic procedure as described above, as contrast media fills the empty pocket 240 of the disc holder 201 and pressure thus builds, the elastomeric valve disc 202 bends and eventually opens the slit 241 (which occurs at a certain pressure, known and referred to herein as the 'cracking pressure') to inject fluid into the valve body. The dimensions of the pocket allow for control of the cracking pressure; at a given pressure, exposing a greater surface of the disc to that pressure will increase the force upon a disc and thus lower the cracking pressure. The situation where the slit opens and fluid flows from the inlet port 222 through the slit into the valve body 203 is shown in more detail in FIG. 3, described below.

Continuing with reference to FIG. 2, in an exemplary embodiment a valve body 203 has two internal tapers. A narrow taper 205 closest to the disc 202 contains the saline port, and a second wider taper 206. In operation, the narrow taper next to the disc 202 allows the saline/transducer port 220 to be sealed as pressure builds up and before fluid passes through the disc 202. The second, wider taper 206 and associated cavity create room for the disc to expand and allow the slit 241 to open fully. The converging angles (in the forward flow direction) also promote flushing of air from the valve so that no bubbles are left behind.

Figure 3:
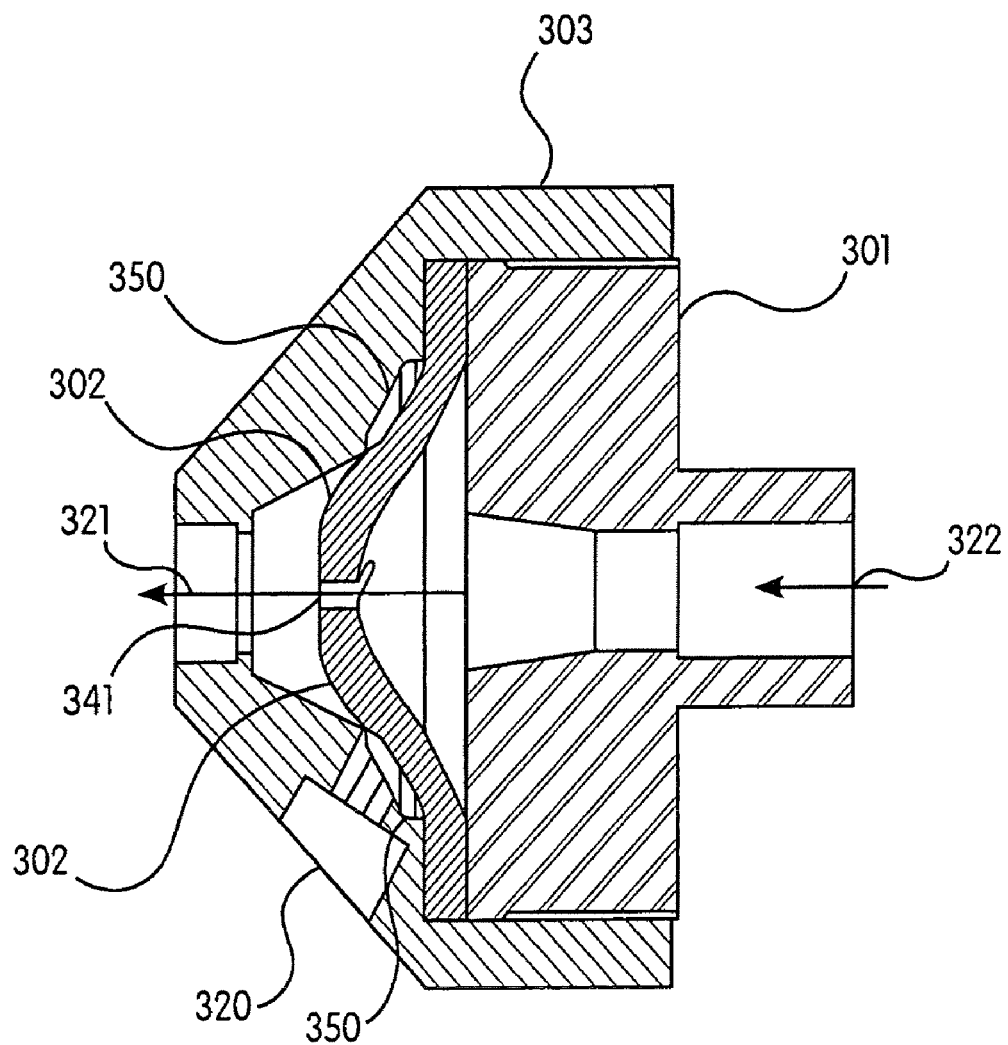
FIG. 3 is a cross sectional view taken along a direction normal to fluid flow of the exemplary valve assembly of FIG. 1 depicting the open (high pressure) mode of operation.

FIG. 3 depicts the exemplary valve of FIG. 2 in the high pressure fluid flow state described above. With reference to FIG. 3 contrast fluid under high pressure flows through inlet port 322. This has caused the pressure applied to the right side of the disc 302 to exceed the 'cracking pressure', which caused disc 302 to expand in the direction of flow (or to the left in FIG. 3), opening the disc slit 341. As the disc expanded it covered the opening of the saline/transducer port 320 in the cavity of the valve body 303. At the same time, the force maintained on the disc 302 by the incoming fluid keeps the saline port shut during high pressure fluid flow, such as, for example, is experienced in a contrast fluid injection. The first taper has, for example, a ring-shaped channel 350 where the saline port 320 is located, thus allowing the interior of the valve body 303 to be completely filled with saline during initial setup. In an exemplary embodiment, the rest of the valve body 303 and the corners of the channel are preferably rounded to eliminate any trapping of air bubbles during setup and. Also, such a channel helps air to be removed by a vacuum applied manually using a syringe.

In exemplary embodiments, the valve can be used in connection with low pressure to high pressure medical fluid injections. It can also be used with CT, MRI and cardiology contrast media injection systems. Additionally, a two-port version of the valve with the elimination of the saline/transducer port 320 can be manufactured economically enough to act as a check valve. Such a high/low pressure valve is thus inexpensive to manufacture, having a simple design and consisting of three molded parts that can be assembled and bonded together.

The disc holder contains the fluid inlet port and, in exemplary embodiments, can be molded or machined out of, for example, polycarbonate, PET, acrylic or any other tough polymer as may be known in the art that can withstand high pressures. In exemplary embodiments of the invention the elastomeric disc 202, 302 is preferably circular and may be, for example, molded or cut from sheet silicone rubber or other elastomers including, for example, polyurethane and latex. In exemplary embodiments, properties of an elastomeric disc material are, for example, a durometer in the range of 40-70 A, more specifically, for example, 55 A, a tensile strength of 1000-1500 psi, an elongation of 300-700%, and a tear strength 150-300 lbs./inch. In an exemplary embodiment, the disc may be 0.060" thick or may have a range of 0.020" to 0.200" in thickness depending on the durometer, fluid and slit dimensions. In an exemplary embodiment, the slit in the middle of the disc is preferably 0.125" long, and may be 0.050"-0.30" in length. In exemplary embodiments, the disc has a preferred working surface diameter of 0.580" and may range from 0.250" to 2.00".

The valve body 203, 303 is molded or machined out of, for example, polycarbonate, PET, acrylic or other tough polymers that can withstand high pressures (such as, for example, up to 1500 psi). In exemplary embodiments it contains the fluid outlet port 221, 321 and the saline inlet/transducer port 220, 320. In exemplary embodiments the internal shape of the valve body has two tapers 205, 206, the first taper being at an angle from the vertical (i.e., from a plane that is normal to the fluid flow direction, and substantially parallel to the plane the disc surface is in when the disc is non-distended as in FIG. 2) of, for example, 10 degrees-45 degrees, and in an exemplary embodiment 20 degrees, with a width of, for example, 0.020"-0.500", and in a preferred exemplary embodiment 0.115". In exemplary embodiments the saline inlet/transducer port 220, 320 is located in the first taper so that the taper enables the disc 202, 302 to close the saline port 220, 320 when fluid flows from the injection system. In exemplary embodiments the second taper may be at an angle upward from the vertical (as above), for example, 45 degrees-90 degrees and preferably 0.161" deep (depth being measured along the direction of fluid flow) to create space for the disc to expand and the slit 241, 341 to open for passage of fluid through the disc.

In exemplary embodiments the valve is assembled by placing a disc 202, 302 in the valve body 203, 303. Then the disc holder 201, 301 is placed into the valve body 203, 303 and the two parts are, for example, pressed together mechanically or threaded together and either UV-bonded, sonic welded or attached by any equivalent means as may be known in the art. The disc is thus trapped between the valve body and the disc holder all along the disc's outer edge to prevent leaks. In exemplary embodiments the three fluid ports may have, for example, male or female luer threads to conveniently attach to the injection system, patient catheter and saline/transducer system.

Thus, the disc valve accommodates both high and low pressure fluid systems. Also more than one port can be provided in the valve body 203, 303, and can thus be closed or opened during injection, e.g. up to 4 saline-type ports and can be used for different purposes, such as drug injection, patient fluid sampling and a separate pressure transducer. For example, during a high or low pressure injection (although high enough to exceed the cracking pressure) all such ports can be simultaneously closed, and when the injection system is OFF all such ports will be open, or "ON" and can be used simultaneously or as required.

Figure 4:
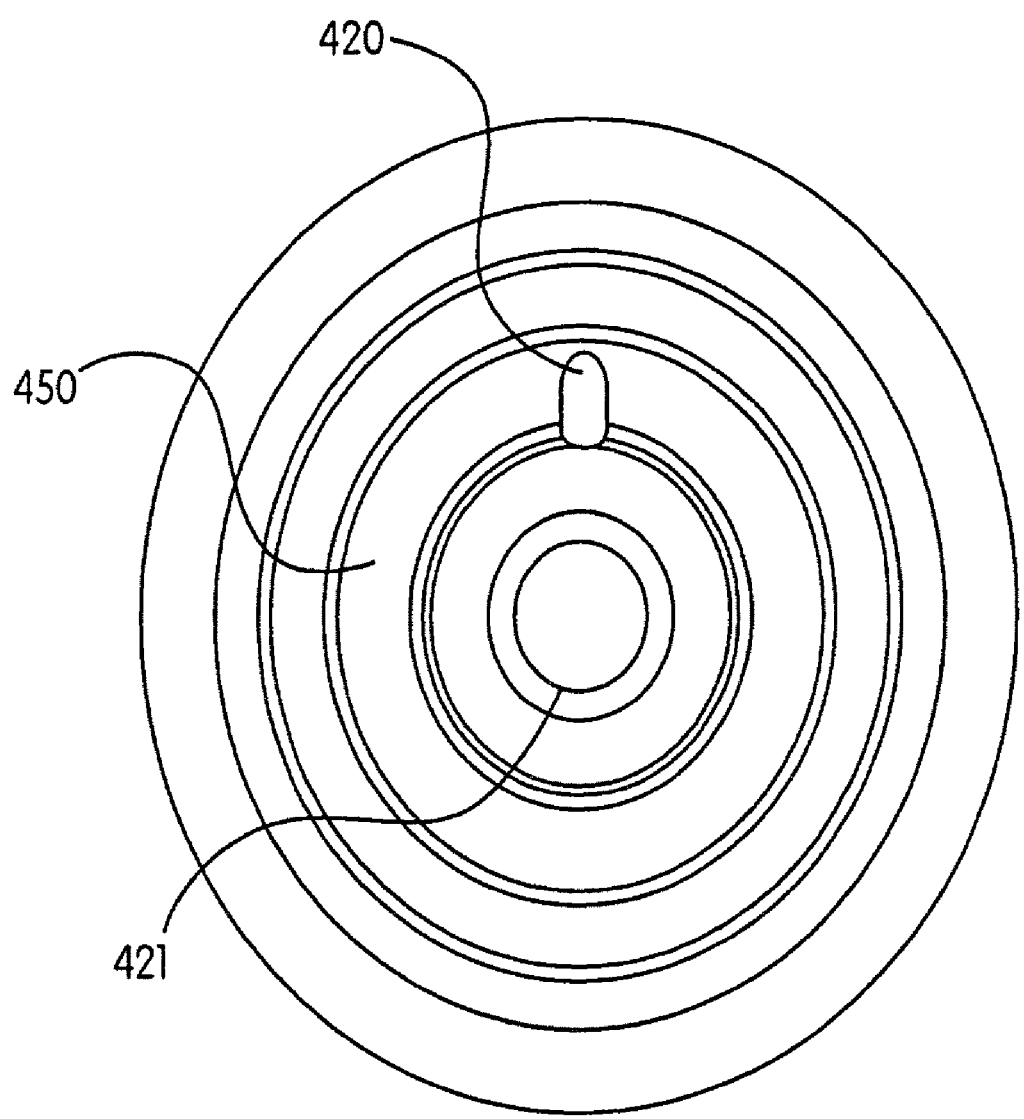
FIG. 4 is a frontal view of the exemplary valve assembly of FIG. 1.

FIG. 4 is a head-on view looking into the contrast fluid output port against the direction of fluid flow. With reference to FIG. 4, besides the contrast fluid output port 421, there can be seen the channel 450, which is an annular ring whose center is the center of the contrast fluid output port and which is positioned relatively close to the edge of the valve disc (unseen in FIG. 4). As was described in connection with FIG. 3, within the channel 450 is the one or more saline/pressure transducer ports 420.

Figure 5:
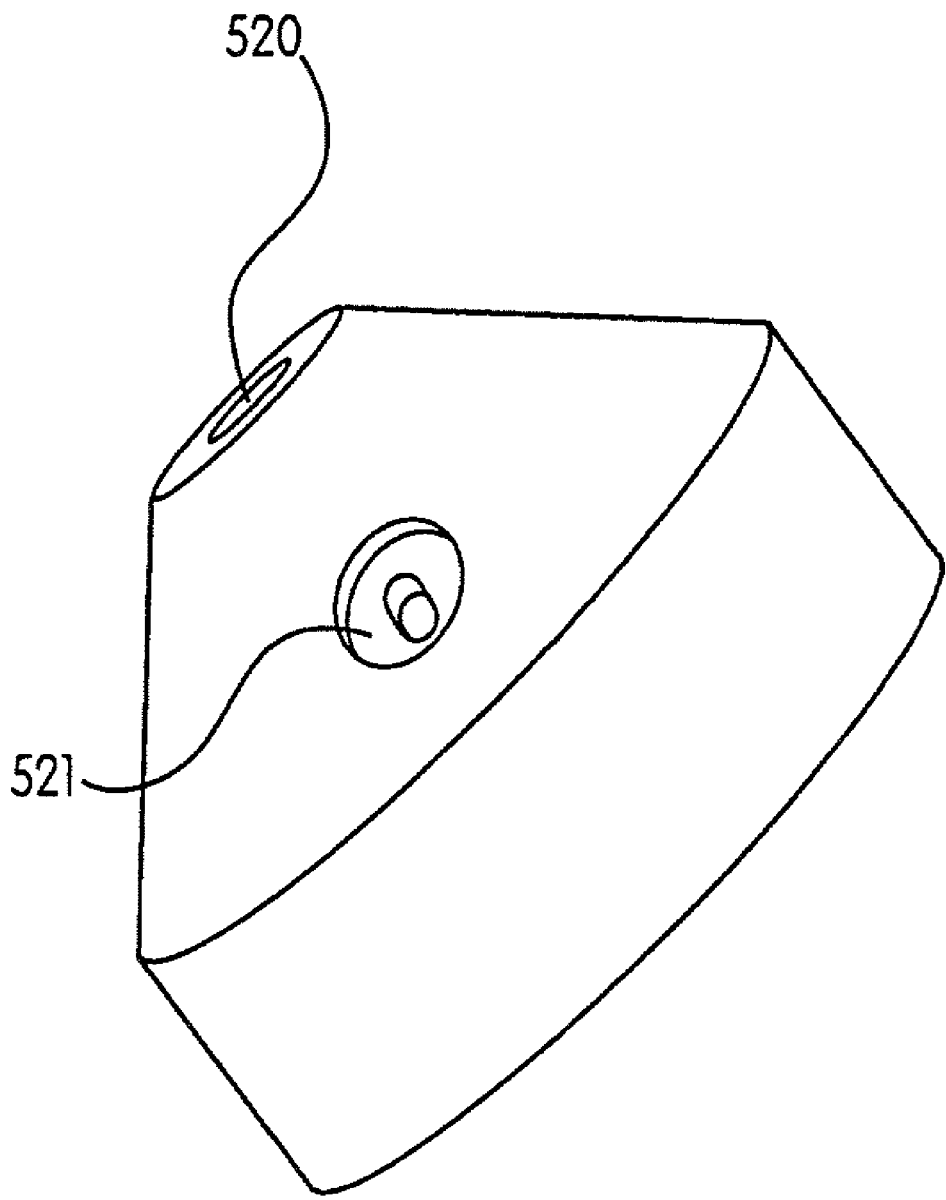
FIG. 5 is a perspective view of an exemplary valve body according to one embodiment of the present invention showing the saline and output ports.

FIG. 5 is a perspective view of the valve body (103 with respect to FIG. 1) showing the contrast fluid output port 521, as well as a saline port 520. It is understood that numerous saline ports could be placed anywhere within the channel (450 with respect to FIG. 4; 350 with respect to FIG. 3) as shall be described below.

Figure 6:
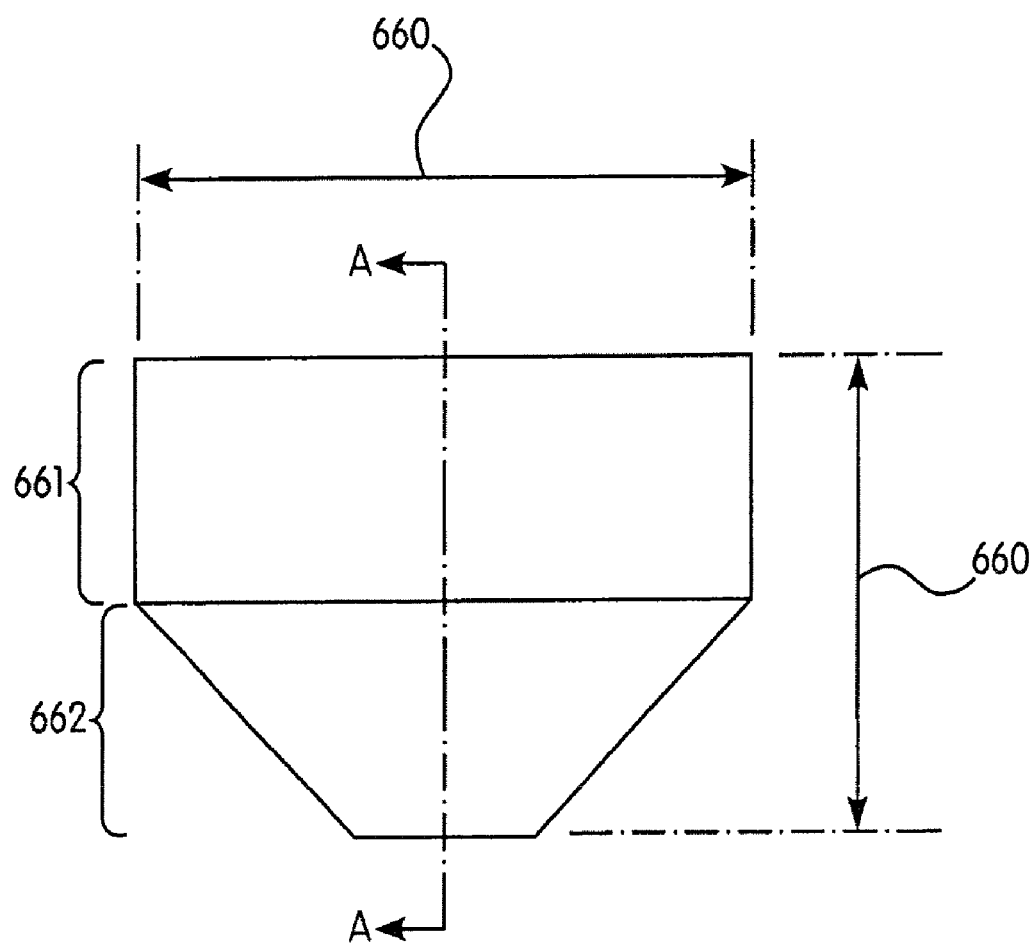
FIG. 6 is a top view of the exemplary valve body of FIG. 5.

FIG. 6 is a top view of the valve body 103 and in the exemplary embodiment depicted in FIG. 6 are shown some representative exemplary dimensions. The overall diameter of the valve body 601 is shown to be one unit, the diameter of the contrast fluid output port 621 is shown to be 0.3 units, overall depth 660 (measured herein along the direction of fluid flow) is shown to be 0.700 units, and the depth of the non-tapered portion of the valve body 661 as 0.35 units. It is understood that the dimensions in FIG. 6 are merely exemplary, and thus show an example of a relationship between the various dimensions of this apparatus. Numerous other dimensions and relationships therebetween are possible and may in fact be desirable, depending on the context and properties of the device that are desired to be accentuated or diminished. For example, the depth of the tapered region 662 is one parameter that controls the cracking pressure. The more room there is in a cavity on the side of the valve disc, the easier it is for the valve disc to be pushed forward (there being less resistance provided by air in a cavity than other possible components), and the lower the cracking pressure. Thus, there is an inverse proportional relationship between the depth 662 and the cracking pressure ("CP"). The greater the area through which a given pressure acts on the disc, the greater the force acting on the disc. Thus CP=k/depth, for some unit determined constant k.

Figure 7:
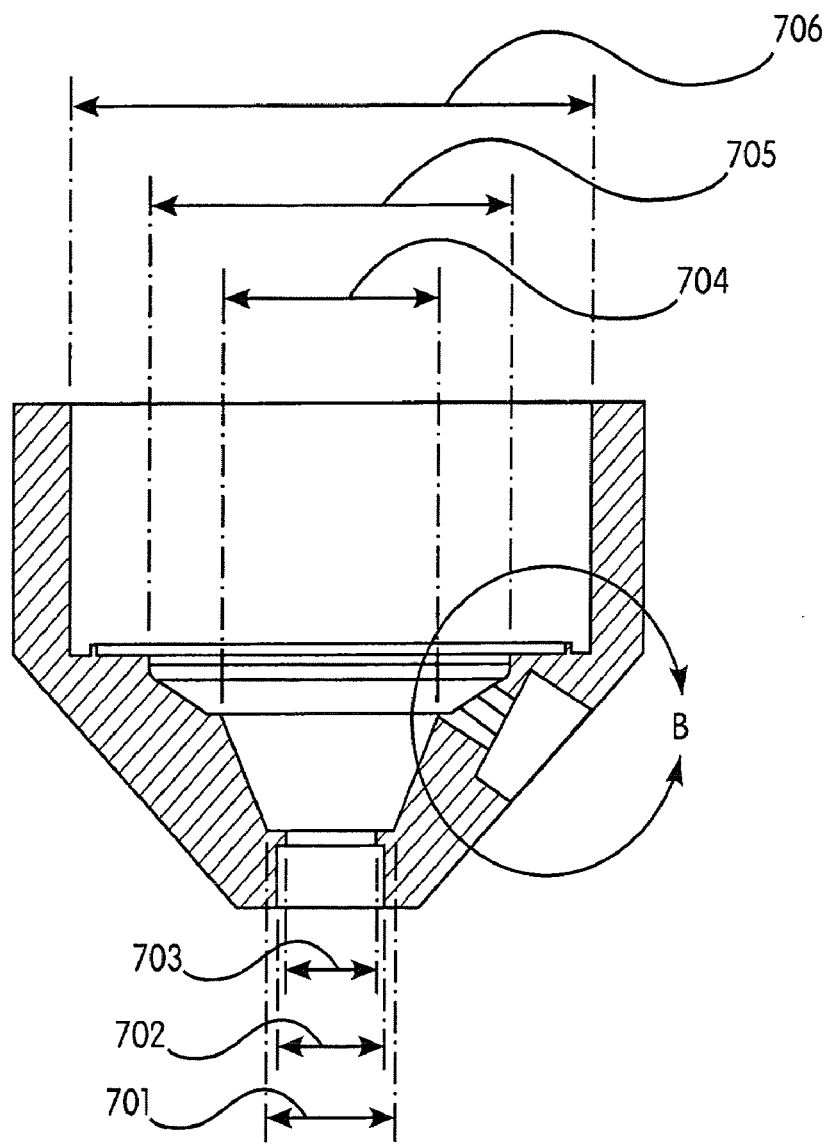
FIG. 7 is a cross section taken at the position A-A of the exemplary valve body of FIG. 6.

FIG. 7 depicts a cross-section along the line A-A of the exemplary valve body depicted in FIG. 6. With reference to FIG. 7, a number of exemplary design dimensions are displayed, such as the inside diameter of the contrast medium output port 701; the outside diameter of that output port 702; the diameter of the cavity at the front edge where the cavity connects into the contrast fluid output port 703; the diameter at the beginning of the second tapered region in the valve body cavity 704; the diameter at the beginning of the first tapered region in the valve body cavity 705; and the inside diameter of the valve body in the non-tapered region 706, which is the diameter into which a given valve disc will fit. As described above, so as not to have any liquid leakage, the diameter of an exemplary disc designed to fit within the diameter 706 will have that same diameter to ensure a tight fit. It is also possible to make the diameter of the disc slightly larger in alternative exemplary embodiments, thus ensuring a tight fit, where liquids of very low viscosity are used which require a greater attention to leakage prevention.

Figure 8:
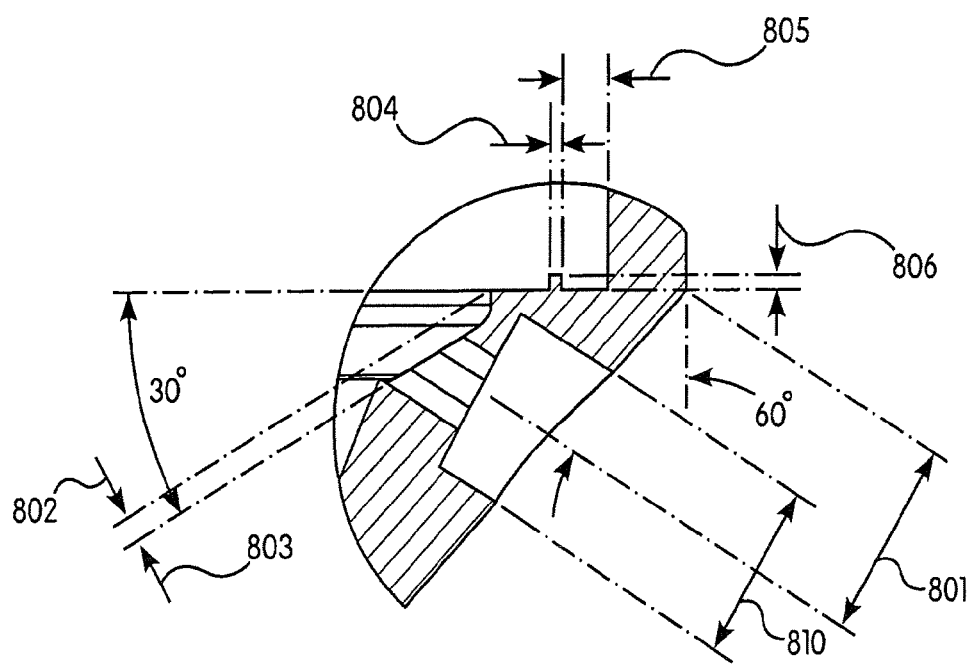
FIG. 8 is a detail drawing of the indicated portion (B) of FIG. 7.
Figure 9D:
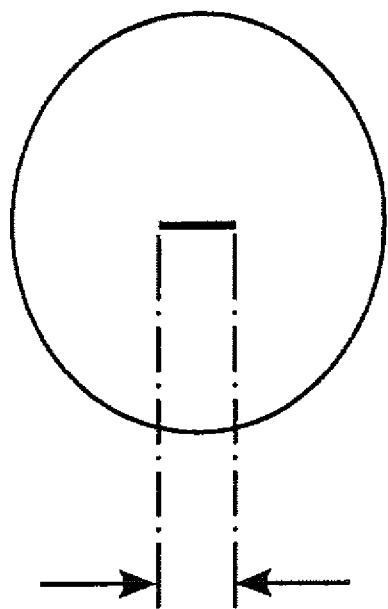
FIGS. 9(d) and 9(e) depict different views of an exemplary valve disc according to one embodiment of the present invention.
Figure 9D:
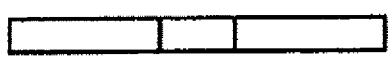
Figure 9E:
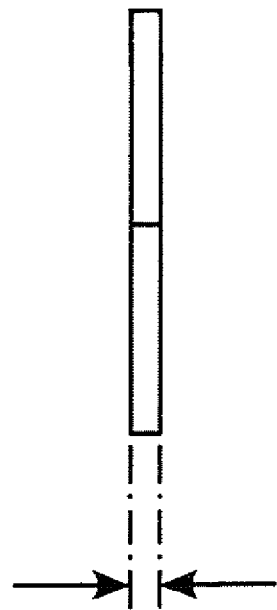

It is noted that for the exemplary embodiment depicted in FIG. 7, an exemplary valve disc designed to fit therein is depicted in FIG. 9(d) in horizontal top view and in FIG. 9(e) in a vertical side view showing. With reference to FIG. 9(d) it can be seen that the diameter of the depicted exemplary valve disc is 0.83 units, identical to the dimension depicted in FIG. 7 element 706. As can be seen with reference to FIG. 7, there is a region 750 depicted as being surrounded by a circle labeled "B." This region is depicted in FIG. 8, as shall next be described.

FIG. 8 depicts the detailed B region in a scale magnified by a factor of 6 relative to FIG. 7. The area of detail depicted in FIG. 8 is, as should be obvious to the reader, the exemplary saline port within the valve body. With reference to FIG. 8, it can be seen that the outer taper of the valve body is, in this exemplary embodiment, 60 degrees off of the vertical and that the distance from the corner where the outer tapered region begins in the outer surface of the valve body to the center of the saline port is, in this exemplary embodiment, 0.192 units 801. Also, angle 802, which represents the angle of the inner taper or the first taper 205 (with reference to FIG. 2) is shown to be 30 degrees in this exemplary embodiment. The exemplary diameter of the saline port 810 is 0.169 units. As well, with reference to FIG. 8, 803 indicates channel depth to manually purge air from the transducer side of the system (which does not require if it is auto purged), 804 a primary taper of a valve body to shut a saline/transducer port during an injection, 805 a location of an indent to clamp a valve disc positively, and 806 a height of an indent for clamping a disc.

With reference to FIGS. 9(a) through 9(c), there are depicted various views of the disc holder 101 (with reference to FIG. 1) in the following exemplary dimensionalities. With reference to FIG. 9(a), an exemplary outward diameter 901 is 0.83 units. It is noted that this dimension corresponds to element 706 in FIG. 7, which is precisely the exemplary dimension into which the inner diameter of the non-tapered portion of the valve body into which the disc holder is to fit. As well, index numbers 902-905 represent exemplary inner diameters of the depicted exemplary disc holder, and with reference to FIG. 9(c), 910 shows an exemplary diameter of a main portion of an exemplary disc holder, 911 an exemplary outer diameter of the high pressure input port, 912 an exemplary inner diameter thereof, 914 an exemplary port size for creating sufficient pressure, 915 an exemplary pocket size for creating pressure, and 908 an exemplary pocket angle (from the vertical) for an exemplary pocket.

With reference to FIGS. 9(d) and 9(e), views of and exemplary dimensions for an exemplary valve disc are shown. With reference to FIG. 9(d), as discussed above, an exemplary outer diameter of the valve disc is shown as 0.83 units. The exemplary disc length is shown as 0.15 units. It is noted that given the relationship between the disc length and the diameter of the valve disc, even when the valve disc slit is completely open, there is no concern for leakage at the perimeter of the valve disc.

Thus, one or more additional saline ports could be placed anywhere within the annular ring identified as the channel 350 with respect to FIG. 3, which would identically and simultaneously be closed upon the currents of the configuration of the valve depicted in FIG. 3. With respect to FIG. 9(e), the thickness of the valve disc is shown and an exemplary thickness of the valve disc shown here in this exemplary embodiment having 0.06 units of thickness.

The design parameters are used to set a cracking pressure for the valve, according to one embodiment. In general cracking pressure is a function of disc thickness, slit length, durometer of the elastomeric disc and the primary taper of the valve body. Cracking pressure increases with increasing disc thickness and disc material durometer, and cracking pressure decreases with decreasing slit length of the disc and primary taper of the valve body.

Figure 10A:
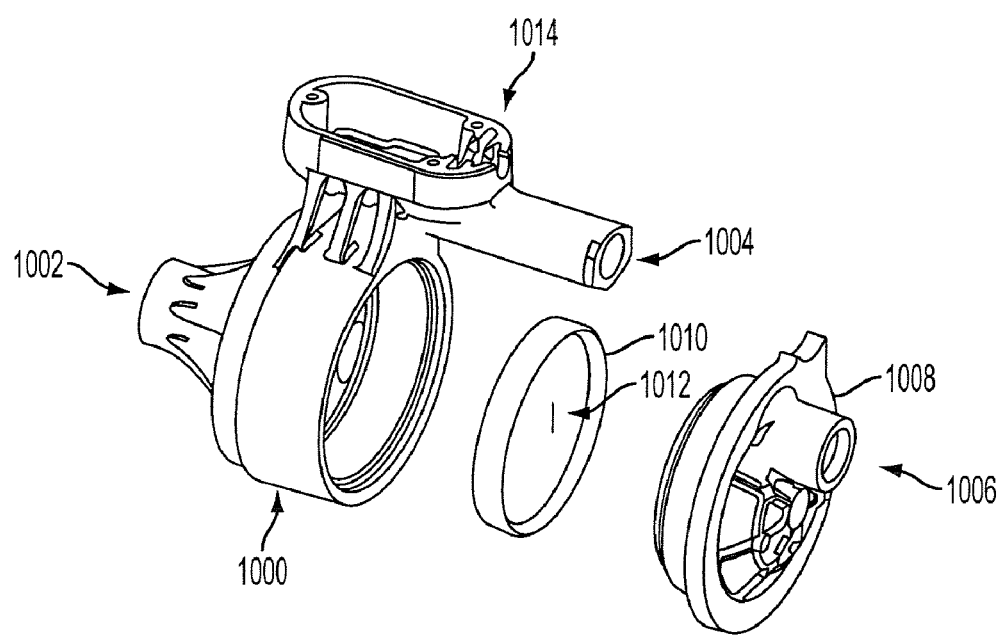
FIGS. 10(a)-10(g) depict various views of an alternate embodiment of a valve assembly.

FIGS. 10(a)-10(g) depict various views of an alternate embodiment of a valve assembly. In this embodiment, the valve assembly includes a valve holder or cover 1008, an elastomeric valve 1010, and a valve body or housing 1000. The assembly also includes a first input port 1006, a second input port 1004, and an output port 1002. FIG. 10(a) shows an exploded view of the valve assembly with each of the separate components 1000, 1008, and 1010. In this embodiment, the first input port is coupled to the valve holder 1008, and both the second input port 1004 and the output port 1002 are coupled to the valve body 1000. In one embodiment, the elastomeric valve 1010 comprises a disc valve.

In one embodiment, the first input port 1006 is aligned along a first axis that is substantially tangent to the valve body 1000. In one embodiment, the first axis is both substantially normal and tangent to the valve body 1000. In one embodiment, the first axis is substantially tangent to a defined area or volume contained within the valve body 1000, and may also be substantially normal to this defined area or volume. FIG. 10(a) and FIG. 10(e) show examples of how this first axis may be substantially normal to a cross-sectional plane of the valve body 1000 (which is also co-planar with the planes through the valve 1010 and the valve holder 1008). These figures also show examples of how the first axis is also substantially tangent to the valve body 1000. This configuration allows fluid that is injected into and through the first input port 1006 to be injected tangentially into and through the valve body 1000 and out of the output port 1002. With this design, the valve assembly provides for an efficient and effective way of purging air (e.g., air bubbles) from the assembly.

In a fluid injection system, air that may be contained within the valve assembly may cause certain problems. For example, air can potentially interfere with and distort heart hemodynamic signals that are sensed or monitored by a pressure transducer, such as a transducer coupled to a transducer port 1014 of the valve assembly. These hemodynamic signals are used by clinicians to safely guide and place the catheter tip coupled to the output port 1002 in safe locations within the heart during a procedure. In addition, there is a risk that any air contained within the valve assembly may potentially be introduced into a patient.

Figure 10B:
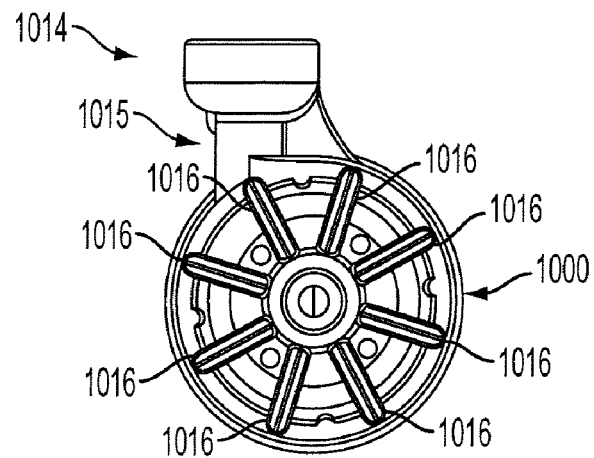

In one embodiment, the second input port 1004 is coupled to a valve input port 1015 (best seen in FIG. 10(b)), the valve input port being aligned along a second axis that is substantially tangent to the valve body 1000. This second axis is substantially perpendicular to the first axis of the first input port 1006, in one embodiment. In one embodiment, the second axis is substantially tangent to a defined area or volume within the valve body 1000. By injecting fluids through the valve assembly by way of the first input port 1006 and the second input port 1004, these fluids can be tangentially injected with relation to the valve body 1000. Tangentially aligned fluid ports, such as the ports 1006 and 1004, cause the medical fluids injected through such ports to follow spiral paths, according to one embodiment. This spiraling fluid flow can sweep air bubbles clinging to the periphery of the valve out an exit port 1020 (best seen in FIG. 10(c)). This spiraling action may be sufficient to remove air bubbles from the elastomeric valve 1010 in any orientation of the valve assembly. By improving the efficiency and effectiveness of air removal from within the valve assembly, an improved hemodynamic signal may be provided to a pressure transducer that is coupled to the transducer port 1014 of the valve assembly, and there may also be less chance of air being introduced into the patient.

In one embodiment, the valve holder 1008 comprises a disc holder, and the valve 1010 comprises an elastomeric valve disc. As can be seen best in FIG. 10(a), the valve 1010 includes one or more slits (one such slit 1012 is shown in FIG. 10(a)). In this embodiment, the slit 1012 is centered within the valve 1010. When the elastomeric valve 1010 is in a closed state, the first input port 1006 is isolated from the output port 1002 and the second input port 1004 (along with the pressure transducer that may be connected to the transducer port 1014). In this state, fluid may not flow from the first input port 1006 to the output port 1002, but fluid (such as a diluent, saline) may flow from the second input port 1004 to the output port 1002, and a pressure transducer coupled to the transducer port 1014 may be capable of detecting an monitoring hemodynamic signals from a patient line coupled to the output port 1002.

When the elastomeric valve 1010 is in an open state, the second input port 1004 and the transducer port 1014 is isolated from the output port 1002 and from the first input port 1006, while the first input port 1006 then becomes coupled with the output port 1002 for fluid flow. The valve 1010 is in the open state when a fluid pressure into and through the first input port 1006 equals or exceeds a defined pressure and causes the valve to open (such as by causing the slit 1012 shown in FIG. 10(a) to open). In the open state, fluid may flow from the first input port 1006 through the slit 1012 of the valve 1010, into the body 1000, and out of the output port 1002, but the second input port 1004 and transducer port 1014 are blocked from the higher-pressure flow (so as, for example, to protect a pressure transducer connected to the port 1014 from becoming damaged from such high-pressure flow). In such fashion, the elastomeric valve assembly shown in FIG. 10(a) through FIG. 10(e) operates in a similar fashion to the prior embodiments of the elastomeric valve (described previously in the present application).

In one embodiment, the state of the valve (such as the valve disc 1010 shown in FIG. 10(a)) is determined by a pressure applied to the first input port 1006 for incoming fluid. In one embodiment, the defined pressure comprises a cracking pressure of the valve 1010 to cause opening of the slit 1012. In one embodiment, the cracking pressure is a function of at least one of physical properties of the elastomeric valve 1010, interior dimensions of the valve holder 1008, valve body 1000 and/or valve 1010, or exterior dimensions of the valve holder 1008, valve body 1000 and/or valve 1010.

Figure 10C:
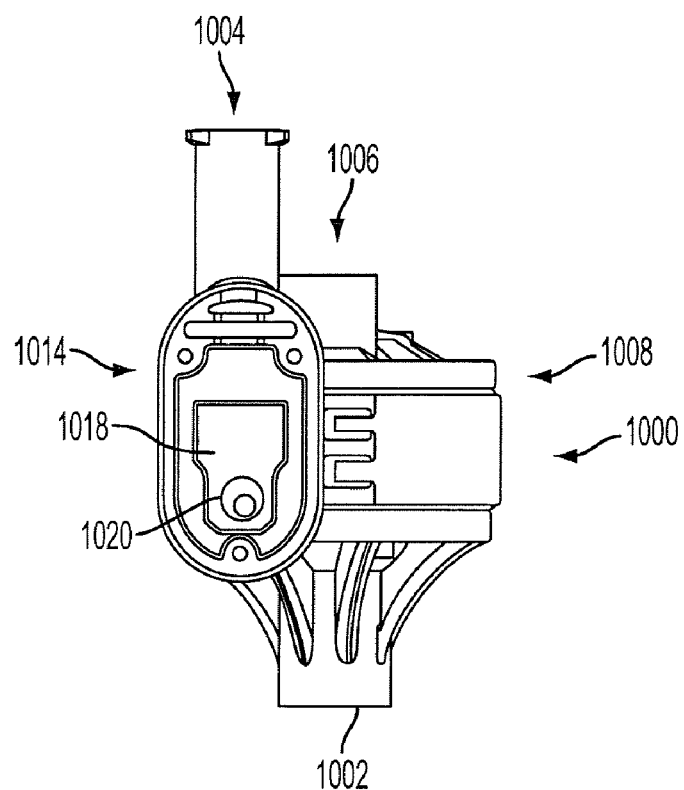
Figure 10D:
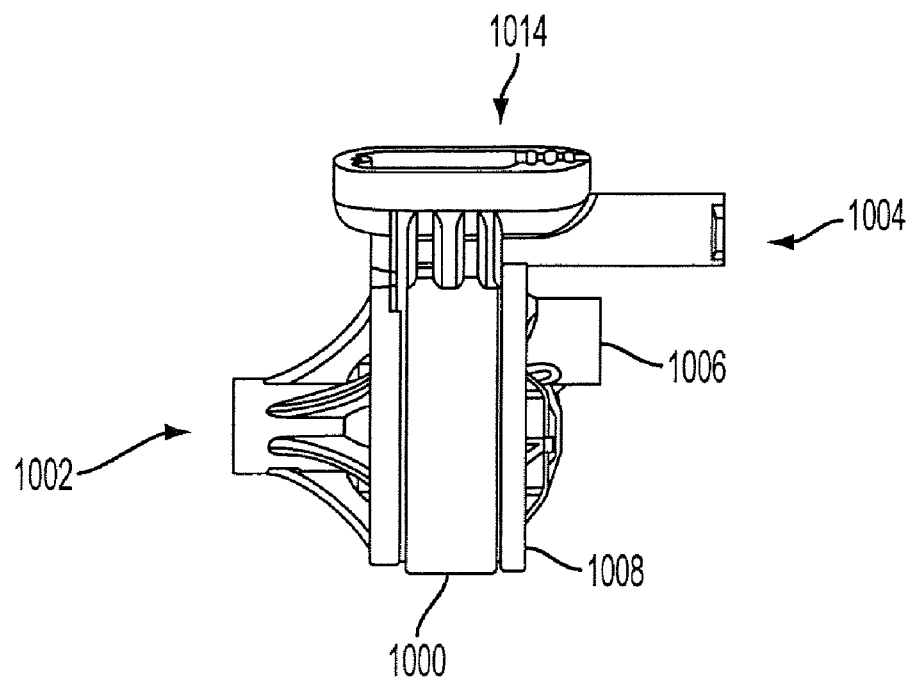
Figure 10E:
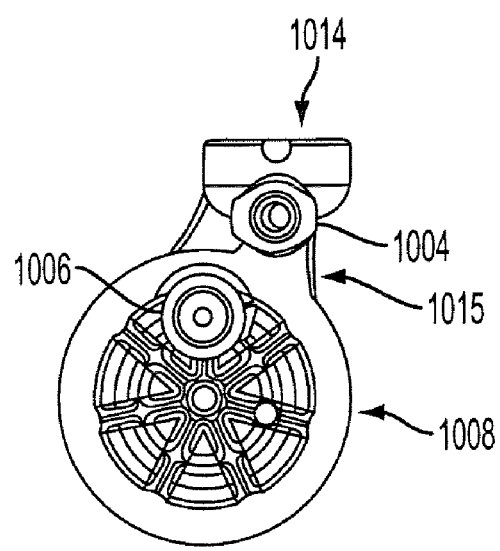
Figure 10F:
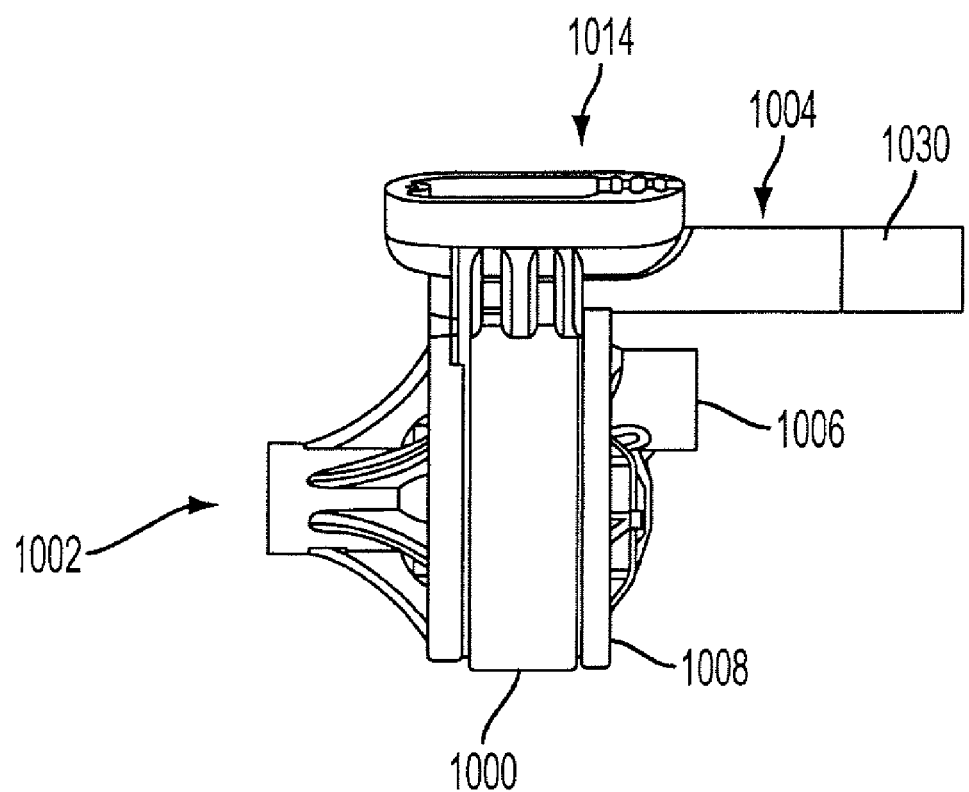

In one embodiment, the second input port 1004 is coupled to a bi-directional check valve 1030, as shown in FIG. 10(f). In some embodiments, duck-bill or spring-based bi-directional check valves may be used. In other embodiments, other forms of bi-directional check valves may be used. The bi-directional check valve 1030 allows fluid flowing from external tubing through said check valve, into the second input port 1004, through the housing 1000 and out of the output port 1002. During a high-pressure injection of fluid through the first input port 1006 and through to the output port 1002, the bi-directional check valve 1030 can further serve to protect a pressure transducer coupled to the transducer port 1014 from high pressures that may potentially damage the transducer. In this type of scenario, the bi-directional check valve 1030 may provide a pressure-relief function, whereby higher pressure can be passed back through the housing 1000, the second input port 1004, the check valve 1030, and out to the tubing that is coupled to the check valve 1030. The tubing may be compliant enough to reduce the over-pressure burden on the transducer. In addition, in certain embodiments, the bi-directional check valve 1030 may provide functionality to reflect hemodynamic signals back towards the transducer, thereby preventing the hemodynamic signal from becoming damped or attenuated.

FIG. 10(b) depicts a front view of the embodiment of the valve assembly shown in FIG. 10(a). As can be seen in FIG. 10(b), the axis through the valve input port 1015 (which is coupled to the second input port 1004 and also to the transducer port 1014) runs in a direction that is tangent to the valve body 1000 (e.g., such as tangent to a defined area or volume within the valve body 1000). FIG. 10(b) also shows that the valve body 1000 includes a number of reinforcement ribs 1016. These reinforcement ribs 1016 help reinforce and support the valve body 1000 for stability. The ribs 1016 help contain high pressures such that the valve assembly does not significantly deform or burst, according to one embodiment.

FIG. 10(c) depicts a top view of the embodiment of the valve assembly shown in FIG. 10(a). This figure shows that the first input port 1004, the second input port 1006, and the output port 1002 may all lie along parallel axes, in one embodiment. FIG. 10(c) also shows the transducer port 1014 in more detail. The transducer port 1014 includes a seat 1018 for coupling a pressure transducer to the port 1014. An exit port 1020 is also shown, which allows air to vent from the valve assembly during use. Possible air bubbles may be purged from the valve assembly through the exit port 1020 during tangential injection of fluid through either or both of the input ports 1004 and/or 1006.

FIG. 10(d) shows an alternate view of the valve assembly shown in FIG. 10(a). FIG. 10(a) shows an exploded view of the components of the valve assembly, while FIG. 10(d) shows a side-view of the assembled/manufactured valve assembly.

FIG. 10(e) shows a back view of the embodiment of the valve assembly shown in FIG. 10(a). FIG. 10(e) shows how fluid injected through the first input port 1006 can be injected along an axis that is both substantially normal and tangent to the valve body 1000 (and also substantially normal to the valve holder 1008). In addition, FIG. 10(e) shows another view of how fluid injected through the second input port 1004 and into, and through, the valve input port 1015 can be injected along an axis (of the port 1015) that is substantially tangent to the valve body 1000.

FIG. 10(f) shows a view of an embodiment of the valve assembly that is coupled to a bi-directional check valve 1030, which was previously described. The bi-directional check valve 1030 is coupled to the second input port 1004.

Figure 10G:
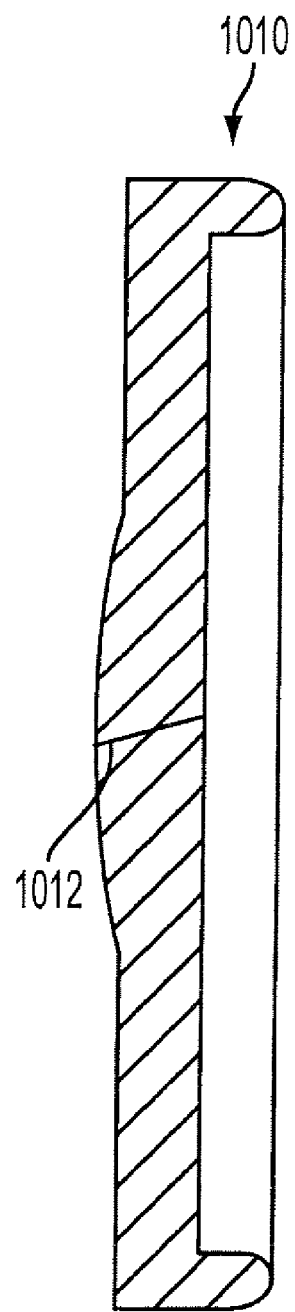

FIG. 10(g) shows a sectional view of the elastomeric valve 1010 shown in FIG. 10(a), according to one embodiment. FIG. 10(g) shows an example of the slit 1012 as being an angled slit. In one embodiment, the angled slit 1012 lies along an axis, wherein the angle between this axis and the horizontal axis of FIG. 10(g) is defined to be in the range of 5 degrees-30 degrees. In other embodiments, different angle configurations may be used. In one embodiment, during fluid injection, the angled slit 1012 may open to allow flow to from an injector, through the valve 1010 and out to the output port 1002 (in a direction of right-to-left in FIG. 10(g)).

Figure 11A:
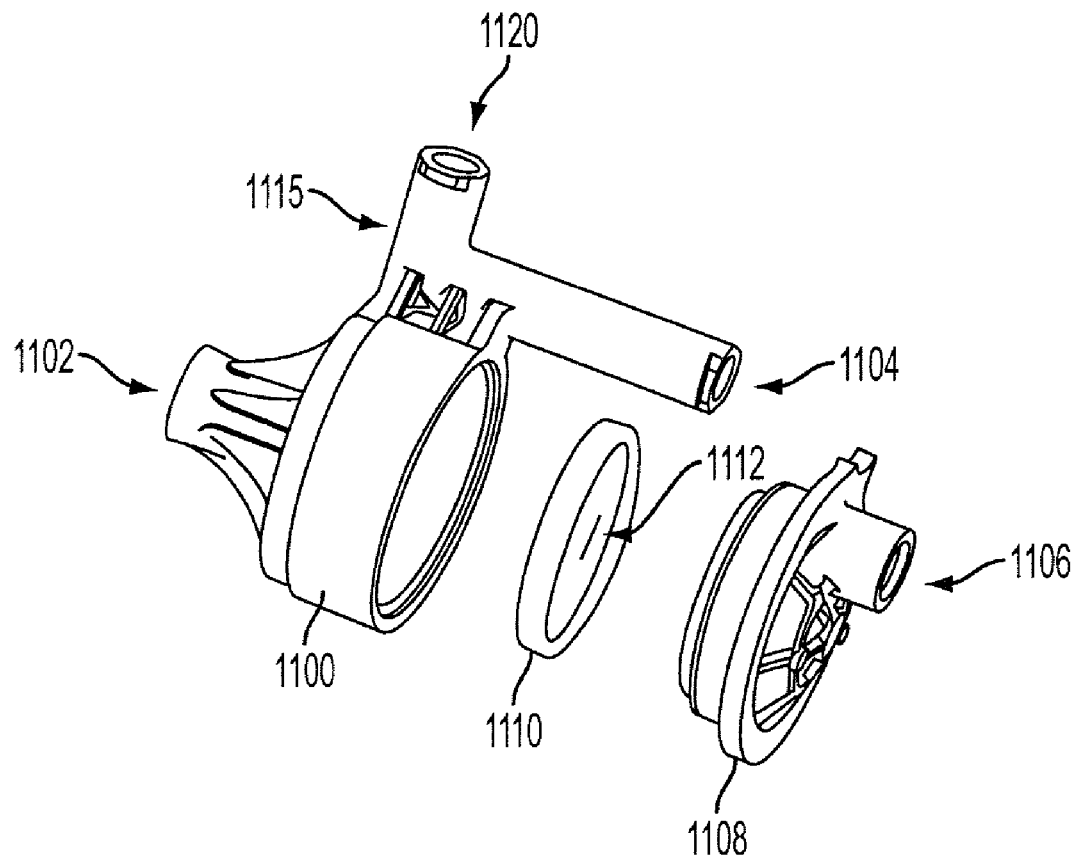
FIGS. 11(a)-11(g) depict various views of yet another alternate embodiment of a valve assembly.
Figure 11B:
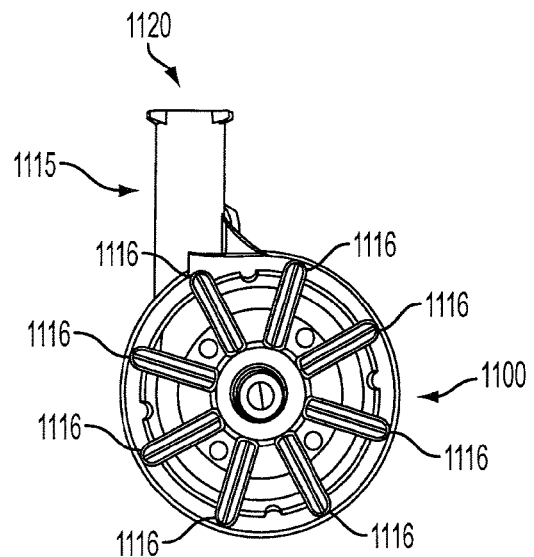
Figure 11C:
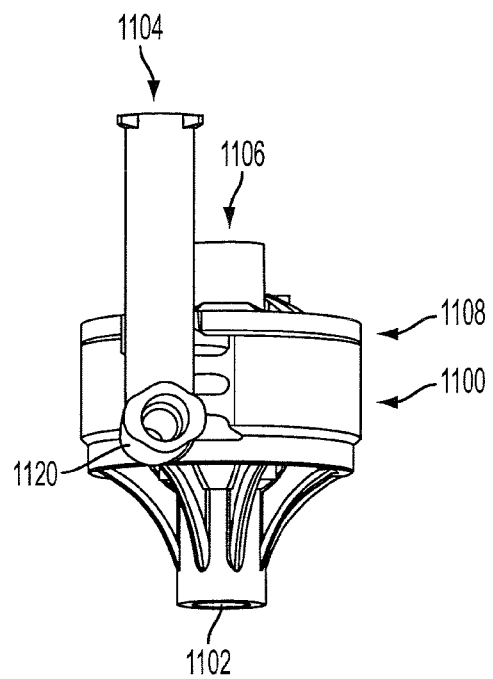
Figure 11D:
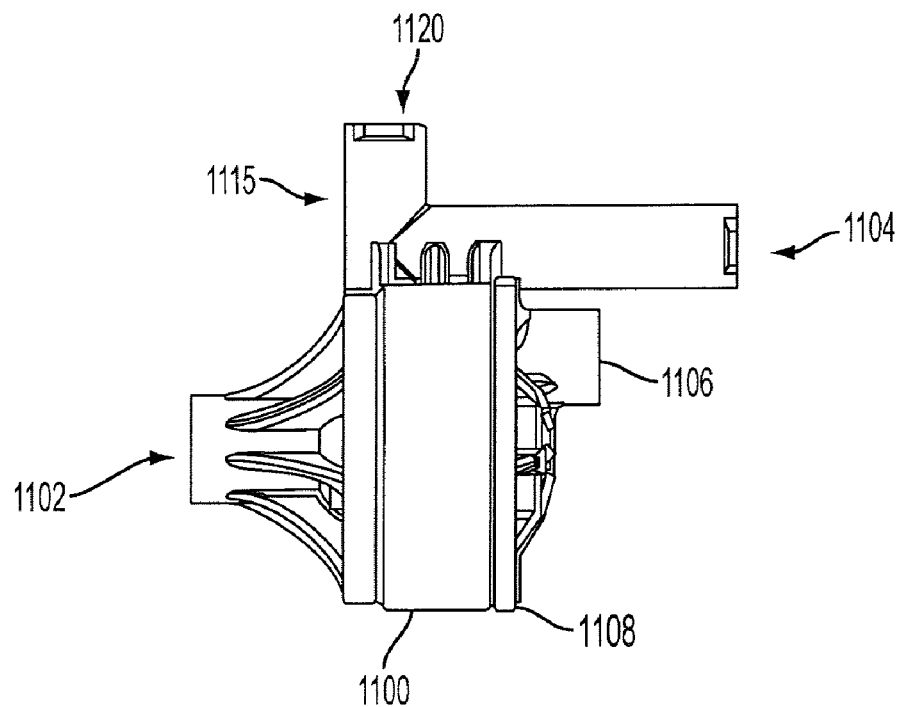
Figure 11E:
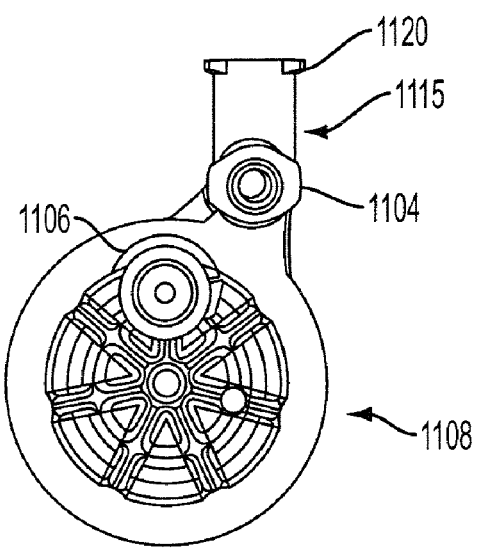

FIGS. 11(a)-11(g) depict various views of yet another alternate embodiment of a valve assembly. This alternate embodiment of the valve assembly is similar to the embodiment shown in FIGS. 10(a)-10(g), but without a pressure-transducer port. FIG. 11(a) shows an exploded view of this alternate embodiment, wherein an exit port 1120 of the valve assembly may be coupled to an external, separate transducer port and pressure transducer. With this design, a user may couple the valve assembly with different types, shapes, or designs of external pressure transducers that may be used with the valve assembly in monitoring hemodynamic waveform signals propogated from the patient and through the valve assembly (via an output port 1102 and the exit port 1120). The alternate embodiment of the valve assembly shown in FIG. 11(a)-11(g) also includes a first input port 1106, a valve holder 1108, a second input port 1104, an elastomeric valve 1110 (such as a disc valve), a slit 1112 (such as a slit centered within the valve 1110), a valve body 1100, an output port 1102, an exit port 1120, a valve input port 1115 (which is coupled to both the exit port 1120 and the second input port 1104), and reinforcing ribs 1116.

Figure 11F:
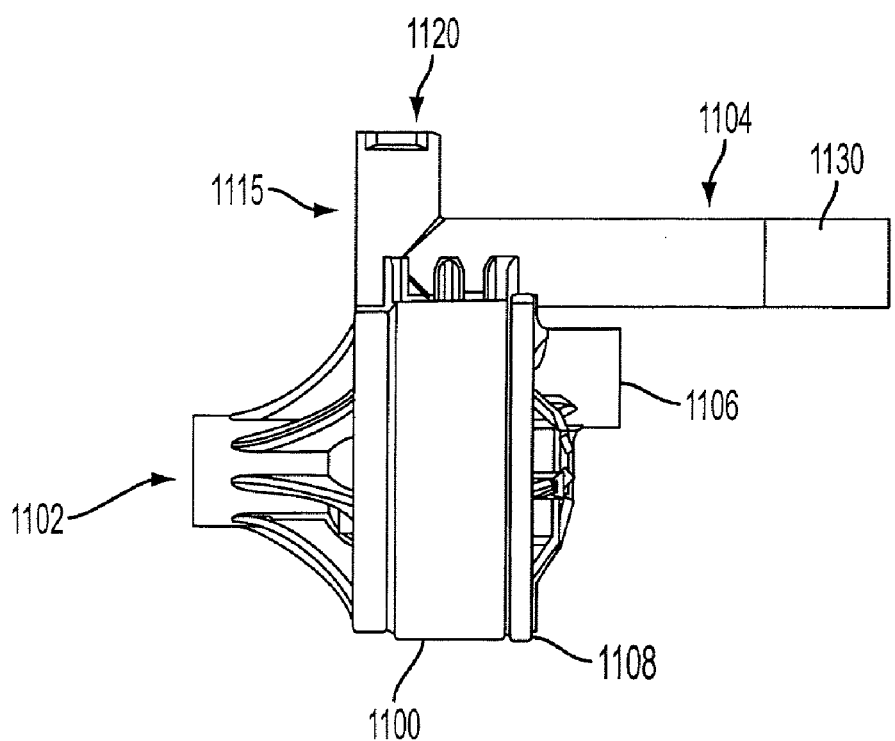

In one embodiment, the second input port 1104 is coupled to a bi-directional check valve 1130, as is shown in FIG. 11(f). In some embodiments, duck-bill or spring-based bi-directional check valves may be used. In other embodiments, other forms of bi-directional check valves may be used. The bi-directional check valve 1130 allows fluid flowing from external tubing through said check valve, into the second input port 1104, through the housing 1100 and out of the output port 1102. During a high-pressure injection of fluid through the first input port 1106 and through to the output port 1102, the bi-directional check valve 1130 can further serve to protect a pressure transducer coupled to the exit port 1120 from high pressures that may potentially damage the transducer. In this type of scenario, the bi-directional check valve 1130 may provide a pressure-relief function, whereby higher pressure can be passed back through the housing 1100, the second input port 1104, the check valve 1130, and out to the tubing that is coupled to the check valve 1130. The tubing may be compliant enough to reduce the over-pressure burden on the transducer. In addition, in certain embodiments, the bi-directional check valve 1130 may provide functionality to reflect hemodynamic signals back towards the transducer, thereby preventing the hemodynamic signal from becoming damped or attenuated.

Figure 11G:
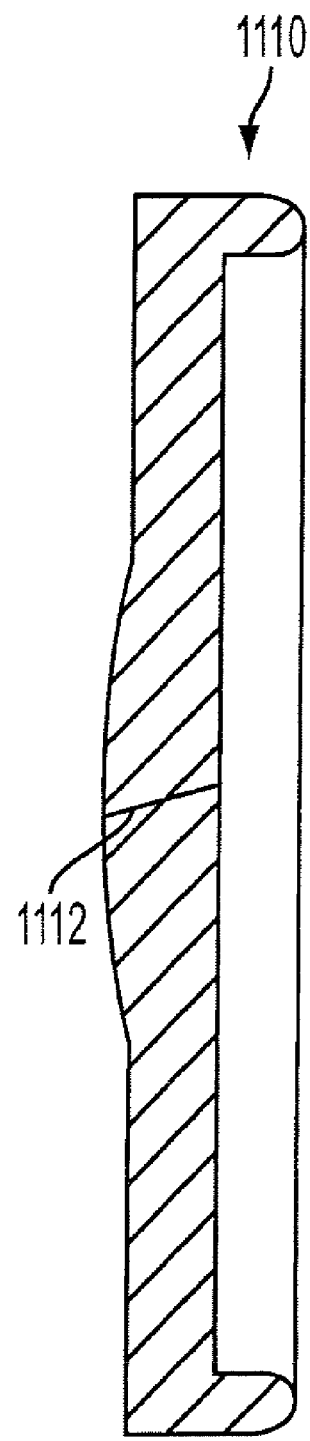

FIG. 11(g) shows a sectional view of the elastomeric valve 1110 shown in FIG. 11(a), according to one embodiment. FIG. 11(g) shows an example of the slit 1112 as being an angled slit. In one embodiment, the angled slit 1112 lies along an axis, wherein the angle between this axis and the horizontal axis of FIG. 11(g) is defined to be in the range of 5 degrees-30 degrees. In other embodiments, different angle configurations may be used. In one embodiment, during fluid injection, the angled slit 1112 may open to allow flow to from an injector, through the valve 1110 and out to the output port 1102 (in a direction of right-to-left in FIG. 11(g)).

The embodiments of valve assembly shown in FIGS. 10-11, along with other embodiments, may provide various benefits. For example, medical fluids (such as contrast media or saline) that are injected into the valve through tangentially aligned fluid input ports help provide spiral fluid flows within the valve. The spiraling fluid flow can help sweep potential air (e.g. air bubbles) within the valve or clinging to the periphery of the valve safely out of the exit port. During fluid injection, there can be high speed fluid flow around the outer edges of the valve and throughout the entire volume of the valve, as well. This can provide certain advantages. For example, enhanced air-bubble removal can potentially be achieved in any elastomeric-valve orientation (depending on the orientation during insertion and use as part of a patient kit in a fluid injection system). This advantage helps minimize the chance that air will be introduced into a patient during a medical procedure. In addition, an improved hemodynamic signal integrity can be achieved, wherein hemodynamic signals from a patient can be more effectively and accurately sensed and measured by a pressure transducer and corresponding monitoring system. The hemodynamic monitoring system then can display the waveforms to a clinician to provide accurate feedback about pressure within a patient's vascular system during a procedure. Such information can assist the clinician in many ways, such as to help alert the proper of improper placement of a patient catheter (which can ultimately help reduce the potential incidence of arterial dissection).

Figure 12:
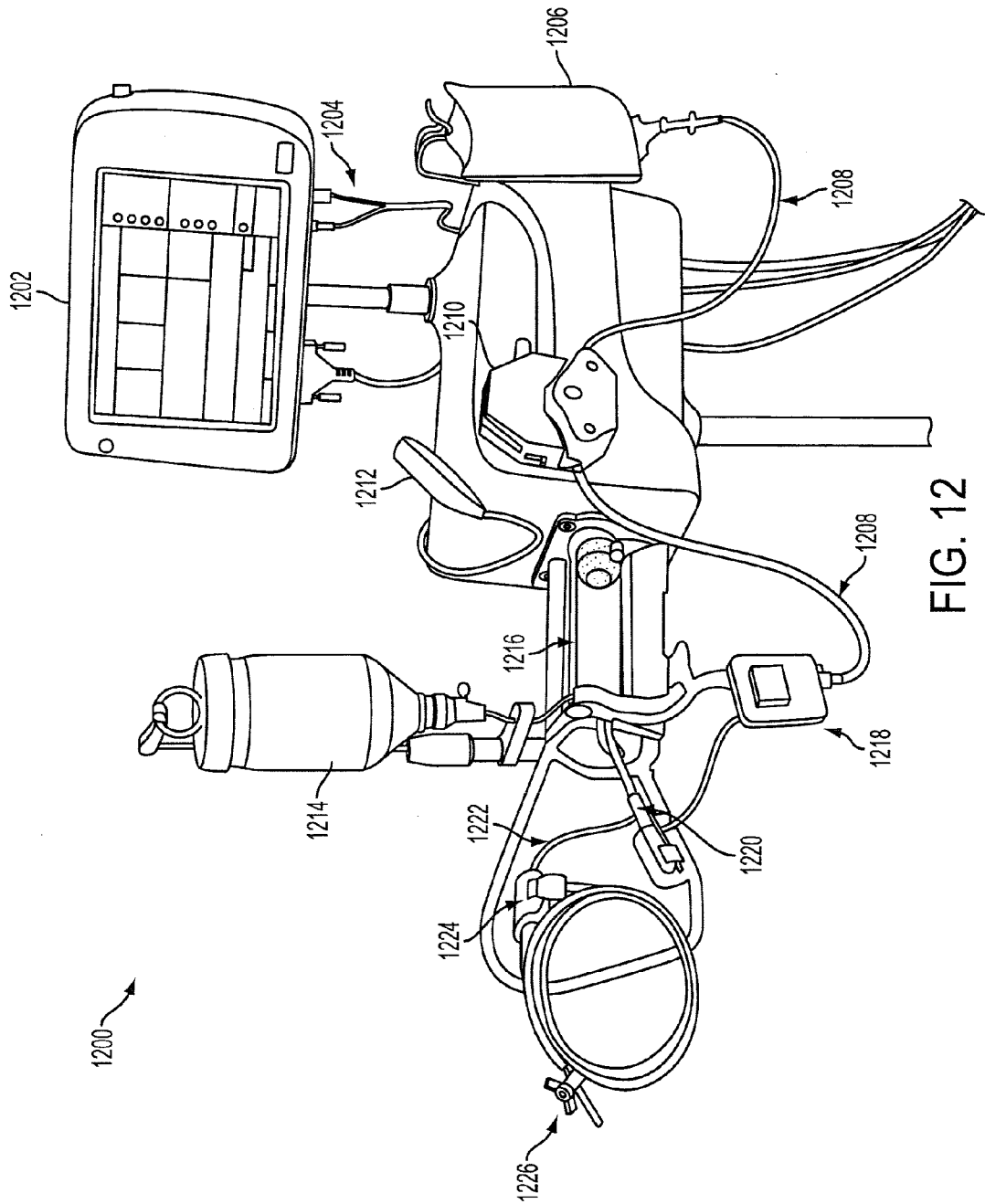
FIG. 12 is a block diagram of one embodiment of a powered injection system that may be used to perform various functions and, when operable, may be coupled to a valve assembly.

FIG. 12 is a block diagram of one embodiment of a powered injection system 1200 that may be used to perform various functions and, when operable, may be coupled to a valve assembly within a medical sterile field, such as an embodiment of a valve assembly described above. The powered injection system 1200 shown in FIG. 12 may be used to inject medical fluid, such as contrast media or saline, into a patient within the sterile field during a medical procedure (such as during an angiographic or CT procedure). A valve assembly, such as an assembly comprising an elastomeric valve, may be coupled to the system 1200 and used within the sterile field during the entire course of a patient procedure, according to one embodiment. The system 1200 includes various components, such as a control panel 1202, a hand-controller connection 1204, a hand controller 1212, a fluid reservoir 1206, tubing 1208, a pump 1210, a pressure transducer 1218, a fluid reservoir 1214, an injection syringe 1216, high pressure injection tubing 1222, a valve 1220, an air detector 1224, and a stopcock 1226. In one embodiment, described in more detail below, the fluid reservoir 1206 comprises a container such as, for example, a bag or bottle of diluent (such as saline), the fluid reservoir 1214 comprises a container such as, for example, a bag or bottle of contrast media, and the pump 1210 comprises a peristaltic pump. In other embodiments, the pump 1210 may comprise other forms of pumping devices, such as a syringe, a gear pump, or other form of displacement pump. In some embodiments, the injection syringe 1216 (along with its associated plunger), which is a pumping device, may be replaced with another form of pumping device that delivers high-pressure fluid injections to a patient. An individual pumping device is capable of operating or functioning in different, or multiple, operational modes. For example, a pumping device may be operable to pump fluid when actuated, or driven, to move in a first direction (e.g., forward), while it may also be operable to move in a second direction (e.g., an opposite direction, backward) to carry out certain functions.

An operator may use the control panel 1202 to set up various parameters and/or protocols to be used during a given procedure. The pump 1210 may be used to pump saline from the bag into the patient via the saline tubing 1208, the valve 1220, and the high-pressure tubing 1222. In one embodiment, the valve 1220 comprises a spring-based spool valve, as is known in the art. In one embodiment, the valve 1220 comprises an elastomeric-based valve, such as an embodiment of an elastomeric valve described in the present application. Various embodiments of the valves disclosed in the present application may be used within the system of FIG. 12.

In one embodiment, the syringe 1216 is used to draw contrast from the reservoir 1214 into the syringe 1216, and to inject contrast from the syringe 1216 into the patient via the valve 1220 and high-pressure tubing 1222. In one embodiment, the syringe 1216 is a self-purging syringe that has one port for filling of contrast and purging of air, and a second port for injection of contrast.

As described above in reference to operation of various embodiments of a valve, the valve 1220 is used to control coupling between input ports to the valve 1220 and the output port. In one embodiment, the valve includes two input ports, one which is coupled to the contrast fluid line and another which is coupled to the saline fluid line. The saline fluid line also includes a pressure transducer 1218.

The stopcock 1226 regulates the flow of fluids to the patient. In one embodiment, the valve 1220 allows either the saline line or the contrast line to be coupled to the patient (high-pressure tubing) line 1222. When the syringe 1216 is used to inject contrast media, the valve 1220 allows the contrast media to flow to the patient line 1222 but blocks the flow of saline to the patient line 1222. The pressure transducer 1218 is also blocked from the patient line 1222 during high-pressure injections, thereby protecting the transducer 1218 from high injection pressures that may accompany a contrast injection. When there is no injection of contrast from the syringe 1216, the valve 1220 blocks the contrast line from the patient line 1222, but opens the connection between the saline line (tubing) 1208 and the patient line 1222. In this state, the pump 1210 is capable of injecting saline into the patient, and the pressure transducer 1218 is also capable of monitoring hemodynamic signals coming from the patient via the patient line 1222, and generating representative electronic signals based upon the measured pressures.

The system 1200 of FIG. 12 also shows a hand controller 1212 and an air detector 1224. An operator may use the hand controller 1212 to manually control injection of saline and/or contrast media. The operator may push one of the buttons on the hand control 1212 to inject saline, and may push the other button to inject contrast. In one embodiment, the operator may push on the contrast button to deliver contrast at a variable flow rate. The harder the operator pushes on the button, the greater the flow rate of contrast media is delivered to the patient. Other controllers, such as foot pedal controllers, may also be used. The air detector 1224 detects potential air bubbles or columns within the high-pressure tubing 1222. In one embodiment, the air detector 1224 is an ultrasonic or acoustic-based detector. In other embodiments, the air detector 1224 may use infrared or other detection means (such as optical). If the air detector 1224 detects the presence of air in the high-pressure tubing 1222, it generates a signal that is used to warn the operator and/or halt an injection procedure.

Figure 13:
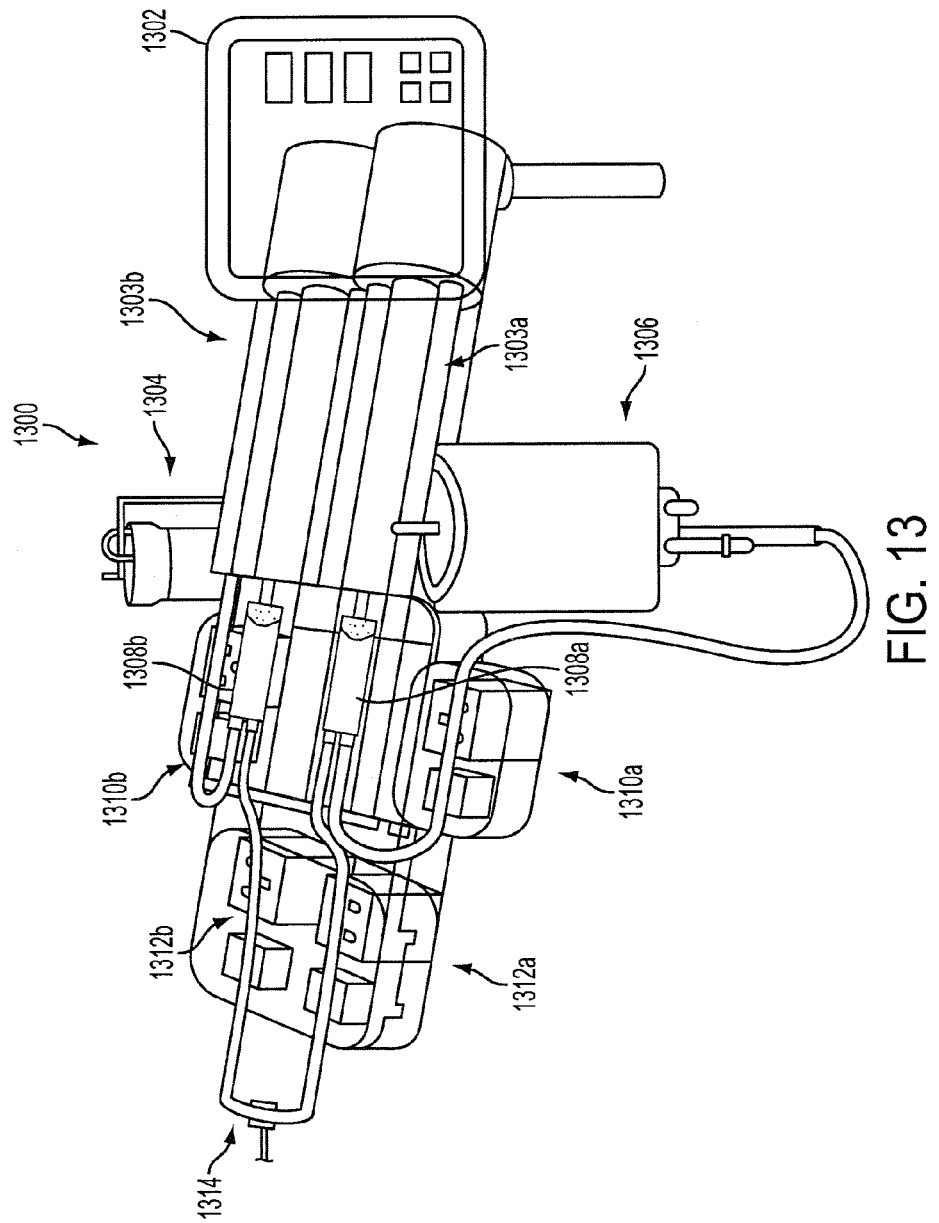
FIG. 13 is a block diagram of another embodiment of a powered injection system that may be used to perform various functions and, when operable, may be coupled to a valve assembly.

FIG. 13 is a block diagram of another embodiment of a powered injection system 1300 that may be used to perform various functions and, when operable, may be coupled to a valve assembly within a medical sterile field, such as an embodiment of a valve assembly described above. The powered injection system 1300 shown in FIG. 13 may be used to inject medical fluid, such as contrast media or saline, into a patient within the sterile field during a medical procedure (such as during an angiographic or CT procedure). A valve assembly, such as an assembly comprising an elastomeric valve, may be coupled to the system 1300 and used within the sterile field during the entire course of a patient procedure, according to one embodiment.

The system 1300 is a dual-syringe system that includes a control panel 1302 and two motor/actuator assemblies 1303a and 1303b. Each motor drives one of the linear actuators in the assemblies 1303a, 1303b. Each linear actuator drives a plunger of one syringe 1308a or 1308b. An individual plunger moves within the syringe barrel of the syringe 1308a or 1308b in either a forward or rearward direction. When moving in a forward direction, the plunger injects liquid into the patient line or purges air out of the syringe and into a liquid container (e.g., bottle). When moving in a rearward direction, the plunger fills liquid into the syringe 1308a, 1308b from a liquid container. FIG. 13 shows examples of two such liquid containers 1304 and 1306. In one embodiment, the container 1304 is a bag or bottle containing contrast agent, and the container 1306 is a bag or bottle containing diluent, such as saline. In other embodiments, the syringes 1308a, 13808b (along with associated plungers), which are each pumping devices, may either separately or together comprise another form of pumping device that is capable of injecting fluids at appropriate flow rates/pressures/etc., such as, for example, a peristaltic pump or another form of displacement pump. An individual pumping device is capable of operating or functioning in different, or multiple, operational modes. For example, a pumping device may be operable to pump fluid when actuated, or driven, to move in a first direction (e.g., forward), while it may also be operable to move in a second direction (e.g., an opposite direction, backward) to carry out certain functions.

Multiple sets of pinch valve/air detect assemblies are shown both FIG. 13. One pinch valve/air detect assembly 1310a is coupled between the liquid container 1306 and a syringe input port of the syringe 1308a, and a second pinch valve/air detect assembly 1312a is coupled between a syringe output port of the syringe 1308a and the patient connection. A third pinch valve/air detect assembly 1310b is coupled between the liquid container 1304 and a syringe input port of the syringe 1308b, and a fourth pinch valve/air detect assembly 1312b is coupled between a syringe output port of the syringe 1308b and the patient connection. In the embodiment shown in FIG. 13, each syringe 1308a, 1308b is a dual-port syringe. Fluid flows and is drawn into the syringe 1308a or 1308b from a container via the syringe input port, and fluid flows out of and is injected from the syringe 1308a or 1308b via the syringe output port.

Each pinch valve is a pinch valve/air detect assembly 1310a, 1310b, 1312a, 1312b may be opened or closed by the system 1300 to control the fluid connections leading to or away from each of the syringes 1308a, 1308b. The air detect sensors in the assemblies 1310a, 1310b, 1312a, 1312b may be optical, acoustic, or other form of sensor. These sensors help detect air that may be present in the fluid connections leading to or away from the syringes 1308a, 1308b. When one or more of these sensors generates a signal indicating that air may be present in a fluid line, the system 1300 may warn the user or terminate an injection procedure. The use of multiple pinch valves within the system 1300 allows the system 1300 automatically, or through user interaction, selectively control the flow of fluid into or out of the syringes 1308a, 1308b by opening or closing fluid tubing. In one embodiment, the system 1300 controls each of the pinch valves. The use of multiple air-detect sensors helps improve the overall safety of the system 1300 by detecting possibly air (e.g., columns, bubbles) within fluid (in the tubing) leading to or away from the syringes 1308a, 1308b. Signals from the air detectors are sent to and processed by the system 1300, such that the system 1300 may, for example, provide a warning, or terminate an injection procedure, if air is detected. In the example of FIG. 13, the fluid tubing first flows through a pinch valve and then flows through an air detector within the assemblies 1310a, 1310b, 1312a, 1312b. In other embodiments, other configurations, ordering, and the like may be used for the pinch valves and air detectors within these assemblies. Moreover, other types of valves may be substituted for the pinch valves.

An operator may use the control panel 1302 to initialize, or setup, the injection system 1300 for one or more injection procedures, and may further use the control panel 1302 to configure one or more parameters (e.g., flow rate, volume of fluid to be delivered, pressure limit, rise time) of an individual injection procedure. The operator may also use the panel 1302 to pause, resume, or end an injection procedure and begin a new procedure. The control panel also displays various injection-related information to the operator, such as flow rate, volume, pressure, rise time, procedure type, fluid information, and patient information. In one embodiment, the control panel 1302 may be connected to a patient table, while being electrically coupled to the main injector of the system 1300. In this embodiment, the operator may manually move the control panel 1302 to a desirable location, while still having access to all functionality provided by the panel 1302.

The system of FIG. 13 also includes a valve 1314 coupled to both output lines coming from the syringes 1308a and 1308b. Each syringe output provides fluid injected through tubing that passes through a pinch valve/air detect assembly 1312a or 1312b and that then leads to an input of the valve 1314. In one embodiment, one fluid line to the valve 1314 also includes a pressure transducer. The valve output port of the valve 1314 is coupled to high-pressure tubing line, which is used to direct fluid to the patient. In one embodiment, the valve 1314 is made of a flexible material, such as an elastomeric material described in various embodiments of an elastomeric valve above. In one embodiment, the valve 1314 is an elastomeric valve, such as an embodiment of a valve described in the present application. The valve 1314 allows one of the fluid lines (e.g., the contrast line or the saline line) to be coupled to the patient (high-pressure tubing) line. When saline and contained are contained within the syringes 1308a and 1308b, respectively, the valve 1314 allows the contrast media to flow from the syringe 1308b to the patient line (assuming the pinch valve in the assembly 1312b is open and there has been no air detected), but blocks the flow of saline from the syringe 1308a to the patient line. The pressure transducer coupled to the saline line (according to one embodiment) is also blocked from the patient line, thereby protecting the transducer from high injection pressures that may accompany a contrast injection. When there is no injection of contrast from the syringe 1308b, the valve 1314 blocks the contrast line from the patient line, but allows a connection between the saline line from the syringe 1306 to the patient line. The syringe 1308a is capable of injecting saline into the patient (assuming the pinch valve in the assembly 1312a is open and there has been no air detected), and the pressure transducer is also capable of monitoring hemodynamic signals coming from the patient via the patient line, and generating representative electronic signals based upon the measured pressures that can be processed by the system 1300.

In one embodiment, a small control panel (not shown) provides a subset of functions provided by the main panel 1302. This small control panel may be coupled to the injector within the system 1300. In one scenario, the operator may use the small panel to manage injector setup. The small panel may display guided setup instructions that aid in this process. The small panel may also display certain error and troubleshooting information to assist the operator. For example, the small panel may warn the operator of low contrast or saline fluid levels in the liquid reservoirs and/or syringes.

Figure 14:
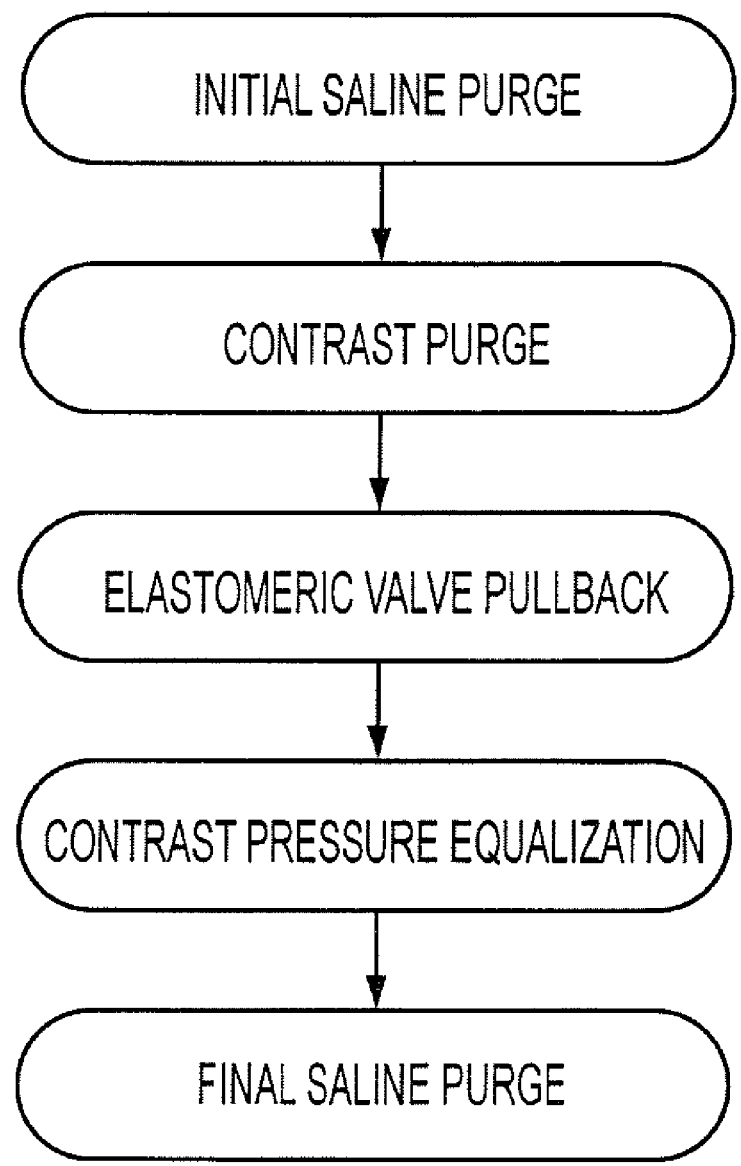
FIG. 14 is a flow diagram of a method that may be performed by a powered injection system, according to one embodiment.

FIG. 14 is a flow diagram of a method that may be performed by a powered injection system, according to one embodiment. This method may be performed by various powered injection systems, such as the system 1200 shown in FIG. 12 or the system 1300 shown in FIG. 13. The ordering of the actions shown in FIG. 14 is for exemplary purposes only. In one embodiment, the powered injection system is capable of performing the method shown in FIG. 14 automatically. In this embodiment, the system may automatically perform the method after the valve and associated tubing are installed, or after the operator has requested that the method be commenced through manual activation on the control or small panel. After the method has been performed, thereby prepping the system, the valve and associated components may be connected to the patient catheter line for use during a patient injection procedure, according to one embodiment.

The powered injection system may first perform an initial saline purge. Initially, the flexible valve, such as an elastomeric valve that may be used in the system, may be filled with air prior to use. Typically, an operator will remove the disposable valve and associated components/tubing from a sterile pouch and connect it to the rest of the injection system. Before the valve is used for a medical procedure, it may contain air that needs to be purged. To help achieve such an air purge, saline is first injected into and through the saline port of the valve by way of a pumping device, such as a peristaltic pump or syringe. In one exemplary embodiment, saline may be injected at a rate greater than 2 ml/sec and with a volume greater than twice the total volume of the valve and its associated disposable tubing. In other embodiments, saline may be injected at lower flow rates. This operation helps clear the air from the front (saline) side of the valve and pressure transducer, which is coupled to the saline line. After the initial saline purge, the front side of the valve can block contrast from flowing back to the transducer element. The connection to the saline pumping device is then closed to preclude additional saline from being injected. For example, in the system shown in FIG. 13, the pinch valve between the saline syringe output port and the flexible (e.g., elastomeric) valve can be closed.

The system also performs a contrast purge operation, according to one embodiment. This is a forceful contrast material injection step that injects contrast from the contrast pumping device (e.g., syringe) into and through the flexible valve on the high-pressure, or contrast, side. In one exemplary embodiment, contrast is injected at a rate greater than 2 ml/sec and with volume greater than twice the total volume of the elastomeric valve volume. In other embodiments, contrast may be injected at lower flow rates. In certain scenarios, a few number of air bubbles from the contrast side of the valve may be transferred to the saline side, and can be removed by a later saline purge act, as described later below.

The next act shown in the example of FIG. 14 is a valve pullback operation (such as when using a flexible or elastomeric valve). During a contrast injection, the flexible valve may bulge and remain partially bulged even when the pressure drops. The pullback operation retracts the valve element to create a larger space on the saline side of the valve. A final saline purge, described below, can then purge any remaining bubbles from the valve. According to one embodiment, care can be taken not to pull back too far or too fast, since this could potentially lead to aspirating air bubbles from the saline side into the contrast side of the valve. Also, vacuum pressures capable of drawing gases out of solution could be generated on the contrast side, as discussed below. The valve pullback operation is performed by retracting the plunger within the pumping device that contains contrast media.

The system may also perform contrast pressure equalization. The elastomeric valve pullback operation can potentially cause vacuum bubbles to form on the back (contrast) side of the valve. If left in this vacuum state, these vacuum bubbles could draw gases from the contrast mixture and form real bubbles. By opening up the fluid coupling (connection) between the contrast bottle (which provides fluid to the syringe) and contrast syringe momentarily, and then closing this coupling after a short delay, the partial vacuum is relieved. (For example, in the system shown in FIG. 13, the pinch valve between the contrast bottle and contrast pumping device may be momentarily opened and then, after a short delay, closed.) The vacuum bubbles can be replaced with contrast from the contrast bottle reservoir.

The powered injection system may also perform a final saline purge, as indicated in the method shown in FIG. 14. In one embodiment, saline may again be injected at rate greater than 2 ml/sec and with volume greater than twice the total volume of the flexible valve and tubing. In other embodiments, saline may be injected at lower flow rates. This operation can clear air from the front side of the valve and pressure transducer on the saline line. The entire valve and tubing may then be cleared of bubbles. At this point, the valve may be safely connected to the patient catheter, according to one embodiment. In the system shown in FIG. 13, all pinch valves are closed before the valve and associated tubing are connected to the patient catheter, according to one embodiment.

When performing the saline or contrast purge operations, the system may cause the saline or contrast pumping devices to operate in certain modes, such as by moving the pumps in specified directions to cause fluid purge to occur. When performing the pullback operation, the system can cause the associated pumping device (such as the contrast pumping device) to operate in other modes, such as by moving the pump in another direction to cause pullback. For example, in either the system 1200 or 1300, the system may cause the contrast pumping device (syringe, as shown in the example) to move in a first direction, but cause the contrast pumping device to move in a second (e.g., opposite) direction to cause pullback of the elastomeric valve.

The method shown in FIG. 14 may provide certain advantages and benefits. For example, the method as performed may provide enhanced bubble removal in any flexible (e.g., elastomeric) valve orientation used in the system. In addition, by performing such a method, a powered injection system can be used to help reduce the possibility that an air bubble potentially located downstream of an air detector will be injected into a patient. The system may also provide improved hemodynamic signal integrity by removing troublesome air bubbles from the fluid line between the patient and the pressure transducer.

Figure 15:
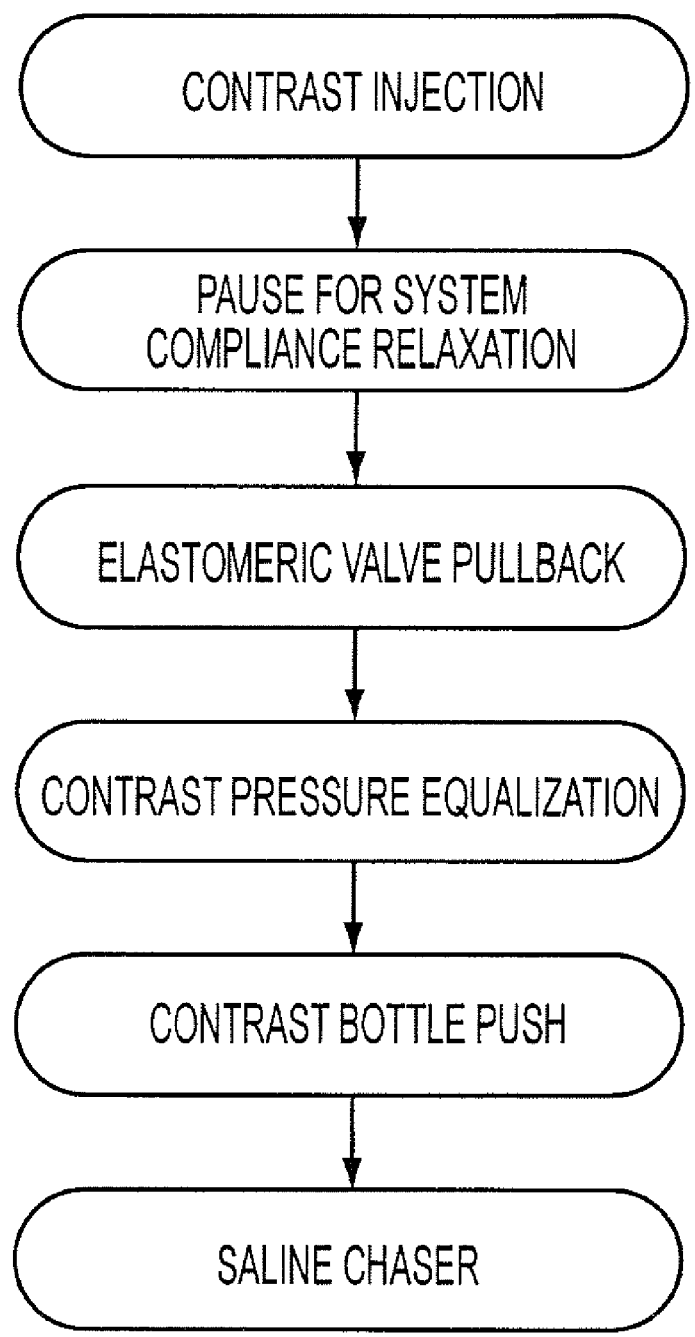
FIG. 15 is a flow diagram of a method that may be performed by a powered injection system, according to another embodiment.

FIG. 15 is a flow diagram of a method that may be performed by a powered injection system, according to another embodiment. This method may be performed by various powered injection systems, such as the system 1200 shown in FIG. 12 or the system 1300 shown in FIG. 13. The ordering of the actions is shown in FIG. 15 is for exemplary purposes only. A contrast injection can consist of as few as one act or many include additional acts, depending upon the particular use and processing of hemodynamic signals in the system. In one embodiment, the powered injection system is capable of performing the method shown in FIG. 15 automatically.

As shown in FIG. 15, an initial act in the method may comprise a contrast injection action. This act includes the forceful contrast material injection that delivers contrast to the location of interest in a patient. The powered injection system performing the method may then, after a given contrast injection procedure, pause for system compliance relaxation. During a forceful contrast injection, flexible components in the contrast fluid path may experience high pressures (e.g., 1200 psi) and expand with the pressure. It may take some time for the expanded components to relax or lose their compliance. As the components relax, the pressure decreases. Before further sequence operations commence, the injection system may pause for a period of time to let the pressure drop. This pause could be a very short interval (even a zero time) or longer if the system requires it (e.g. disposable compliance, tubing compliance, catheter size, etc.).

The system may then perform a valve pullback operation, as shown in FIG. 15. This pullback operation is achieved through operation of the corresponding pumping device, such as by retraction of a syringe plunger in the contrast syringe. The flexible valve, such as an elastomeric valve, allows for forward contrast flow to the patient and prevents backflow. The flexible element also serves a second function by deforming under high pressure flow to seal off a low pressure port on the front (saline) side of the valve and protects the pressure-sensitive hemodynamic transducer element which resides there. During a contrast injection, the flexible element bulges and may remain partially bulged even when the pressure drops back to nominal patient pressure. The partially bulged valve may then partially block the line to the transducer and attenuate higher frequency components of the hemodynamic signal. The pullback operation helps retract the valve element and expose the transducer to the full hemodynamic signal. As the flexible valve is retracted, it expands the volume on the front (saline) side of the valve by a small amount. This small volume can be replaced either by an equal volume of saline or by a full saline chaser, described below, depending upon the need for hemodynamic signal quality.

In some embodiments, the powered injection system may then perform an act of contrast pressure equalization. The valve pullback operation can potentially cause vacuum bubbles to form on the back (contrast) side of the valve. If left in this vacuum state, these vacuum bubbles could potentially draw gases from the contrast mixture and form real bubbles. By opening valves behind the flexible (e.g., elastomeric) valve, such as by opening a fluid connection between the contrast bottle and contrast pumping device, the partial vacuum can be relieved. The vacuum bubbles are replaced with contrast from the contrast bottle reservoir. After a short delay to allow for the vacuum to equalize, the valves behind the flexible valve can again be closed. In some embodiments, the method of FIG. 15 does not necessarily need to include the act of contrast pressure equalization.

The valve pullback operation can also cause vacuum bubbles to form in the contrast pumping device. Small bubbles that were already potentially present in the pumping device may expand under vacuum and consolidate into a larger bubble. A small contrast injection into the contrast bottle may remove this air. Thus, as shown in FIG. 15, a contrast bottle push operation is performed, according to some embodiments. The powered injection system causes the pumping device (such as, for example, by causing the plunger within the contrast syringe to extend a small amount) to push air within the pumping device into the bottle. After a short delay to allow for the pressure to equalize, any valves between the contrast pumping device and bottle can be closed. In some embodiments, the method of FIG. 15 does not necessarily need to include the act of a contrast bottle push operation.

The powered injection system may then perform a saline chase operation. Small diameter catheters, filled with viscous contrast, may attenuate hemodynamic signals. Injecting enough saline to replace the contrast in the catheter with saline enhances the hemodynamic signal. Consequently, the saline chaser volume can be adjusted to catheter size. In one embodiment, the powered injection system is capable of automatically determining the saline chaser volume based upon pre-existing knowledge of catheter size. For example, an operator may initially use the control or small panel to input the catheter size, which can then be later used by the system in determining saline chaser volume. In another scenario, the system is capable of automatically determining catheter size by reading information directly from the disposable catheter tubing being used. For example, the packaging of the catheter tubing may include a bar code that can be read using a bar-code reader installed in the system. The bar code would contain various information about the catheter tubing disposable, including size, that could be used by the system. RFID tags associated with the catheter may also be used to provide information to the system, in one embodiment.

When performing the saline chase or contrast injection operations, the system may cause the saline or contrast pumping devices to operate in certain modes, such as by moving the pumps in specified directions to cause fluid chase or injection to occur. When performing a pullback operation, the system can cause the associated pumping device to operate in other modes, such as by moving the pump in another direction to cause pullback. For example, in either the system 1200 or 1300, the system may cause the contrast pumping device (syringe, as shown in the example) to move in a first direction during injection, but cause the contrast pumping device to move in a second (e.g., opposite) direction to cause pullback of the elastomeric valve.

The method shown in FIG. 15, when performed by an injection system, may provide various benefits and advantages. For example, the use of the system may reduce patient risk caused from improperly positioned catheters. Air bubbles can interfere with and distort heart hemodynamic signals that are being monitored. These signals may be used by clinicians to safely guide and place injection catheter tips in safe locations within the heart. Implementation of the method shown in FIG. 15 (or similar method) can help improve hemodynamic signal integrity by removing air bubbles in the system and/or disposable tubing that is used to deliver fluid to the patient.

The present invention has been described in connection with exemplary embodiments and exemplary preferred embodiments and implementations, as examples only. It will be understood by those having ordinary skill in the pertinent art that modifications to any of the embodiments or preferred embodiments may be easily made without materially departing from the scope and spirit of the present invention as defined by the appended claims.

What is claimed is:

1. A method to purge air or liquid from a powered injection system, the method comprising:
   driving a first pumping device in a first operational mode to inject an amount of a first liquid contrast medium through disposable tubing and a disposable valve having a contrast side and a saline side;
   driving the first pumping device in a second operational mode to deform the disposable valve to create a larger space on the saline side of the valve; and
   driving a second pumping device to inject an amount of a second saline liquid medium through the disposable tubing and the deformed valve, wherein:
   driving the first pumping device in the first operational mode comprises driving the first pumping device in a first direction; and
   driving the first pumping device in the second operational mode comprises driving the first pumping device in a second direction, and wherein the first direction is opposite to the second direction.

2. The method of claim 1, wherein the disposable valve comprises an elastomeric valve.

3. The method of claim 1, wherein:
   the first pumping device comprises a first syringe having a plunger therein; and
   the second pumping device comprises a second syringe having a plunger therein.

4. A method to purge air or liquid from a powered injection system, the method comprising:
- extending a plunger within a first syringe to inject an amount of a first liquid contrast medium through disposable tubing and a disposable valve having a contrast side and a saline side;
- retracting the plunger within the first syringe to deform the disposable valve to create a larger space on the saline side of the valve; and
- upon retraction, extending a plunger within a second syringe to inject an amount of a second liquid saline medium through the disposable tubing and the deformed valve.

5. The method of claim 4, wherein the first syringe and the second syringe are different syringes.

6. The method of claim 4, further comprising:
- prior to retracting the plunger within the first syringe, extending the plunger within the second syringe to inject a second amount of the second liquid saline medium through the disposable tubing and the disposable valve.

7. The method of claim 4, wherein the disposable valve comprises an elastomeric valve.

8. The method of claim 7, wherein the elastomeric valve comprises a first input port coupled to the first syringe, a second input port coupled to the second syringe, an output port, and an elastomeric valve disc.

9. The method of claim 4, further comprising:
- prior to extending the plunger within the second syringe to inject the amount of the second liquid saline medium through the disposable tubing and the deformed valve, momentarily opening a coupling between the first syringe and a fluid reservoir providing fluid to the first syringe; and
- closing the coupling between the first syringe and the fluid reservoir.

10. The method of claim 4, further comprising:
- upon extending the plunger within the first syringe to inject the amount of the first liquid contrast medium through the disposable tubing and the disposable valve, pausing for a period of time.

* * * * *